US010321807B2

(12) United States Patent  (10) Patent No.: US 10,321,807 B2
Alexander et al.  (45) Date of Patent: Jun. 18, 2019

(54) METHODS OF PERFORMING INTERNAL BODY IMAGING

(71) Applicant: TREBLE INNOVATIONS, LLC, Springville, UT (US)

(72) Inventors: Ian Joseph Alexander, Boerne, TX (US); Brian Dean Owens, Plano, TX (US)

(73) Assignee: TREBLE INNOVATIONS, LLC, Springville, UT (US)

( * ) Notice: Subject to any disclaimer, the term of this patent is extended or adjusted under 35 U.S.C. 154(b) by 0 days.

(21) Appl. No.: 15/634,851

(22) Filed: Jun. 27, 2017

(65) Prior Publication Data

US 2017/0290500 A1  Oct. 12, 2017

Related U.S. Application Data

(63) Continuation of application No. 13/303,117, filed on Nov. 22, 2011, now Pat. No. 9,757,150.
(Continued)

(51) Int. Cl.
*A61B 1/00* (2006.01)
*A61B 1/04* (2006.01)
(Continued)

(52) U.S. Cl.
CPC ...... *A61B 1/00108* (2013.01); *A61B 1/00009* (2013.01); *A61B 1/00016* (2013.01);
(Continued)

(58) Field of Classification Search
CPC ............ A61B 1/00016; A61B 1/00032; A61B 1/00064; A61B 1/00066; A61B 1/00071;
(Continued)

(56) References Cited

U.S. PATENT DOCUMENTS 4,545,369 A  10/1985 Sato
4,604,993 A  8/1986 Moriwaki et al.
(Continued)

FOREIGN PATENT DOCUMENTS

WO  2011013733 A1  2/2011

OTHER PUBLICATIONS

"CellScope Launches iPhone Device for Diagnosing Ear Infections", http://block.launch.co/blog/cellscope-launches-phone-device-for-diagnosing-ear-infectio.html [retrieved from the Internet on May 28, 2013], 5 pages.
(Continued)

*Primary Examiner* — Aaron B Fairchild
(74) *Attorney, Agent, or Firm* — Goodhue, Coleman & Owens, P.C.

(57) ABSTRACT

One embodiment provides a system, method, and wireless endoscope for performing internal imaging. A first portion of a wireless endoscope including at least a lens and a light emitter for physical connection to a second portion of the wireless endoscope is received. The first portion is interchangeable. The first portion is inserted into a body while the second portion remains outside the body. The wireless endoscope is powered on in response to receiving user input from a user. A distal end proximate the lens is illuminated utilizing a light in communication with the light emitter. Video inside the body is captured utilizing a camera in communication with the lens. The video is wireless communicated to a receiver associated with a display.

20 Claims, 9 Drawing Sheets

Related U.S. Application Data

(60) Provisional application No. 61/559,190, filed on Nov. 14, 2011, provisional application No. 61/548,596, filed on Oct. 18, 2011.

(51) Int. Cl.

| | | |
|---|---|---|
| *A61B 1/06* | (2006.01) | |
| *A61B 1/233* | (2006.01) | |
| *A61B 17/12* | (2006.01) | |
| *A61B 17/34* | (2006.01) | |
| *A61B 17/24* | (2006.01) | |
| *A61B 34/00* | (2016.01) | |
| *A61B 90/50* | (2016.01) | |
| *A61M 16/04* | (2006.01) | |
| *A61B 90/00* | (2016.01) | |

(52) U.S. Cl.
CPC ...... *A61B 1/00032* (2013.01); *A61B 1/00034* (2013.01); *A61B 1/00066* (2013.01); *A61B 1/00105* (2013.01); *A61B 1/04* (2013.01); *A61B 1/0638* (2013.01); *A61B 1/0676* (2013.01); *A61B 1/233* (2013.01); *A61B 1/00071* (2013.01); *A61B 1/00103* (2013.01); *A61B 1/00154* (2013.01); *A61B 17/12104* (2013.01); *A61B 17/24* (2013.01); *A61B 17/3423* (2013.01); *A61B 34/70* (2016.02); *A61B 34/76* (2016.02); *A61B 90/39* (2016.02); *A61B 2017/246* (2013.01); *A61B 2017/345* (2013.01); *A61B 2017/3447* (2013.01); *A61B 2090/3937* (2016.02); *A61B 2090/502* (2016.02); *A61B 2217/005* (2013.01); *A61M 16/0488* (2013.01); *A61M 2209/088* (2013.01); *A61M 2210/0618* (2013.01)

(58) Field of Classification Search
CPC ............ A61B 1/00009; A61B 1/00108; A61B 1/00163; A61B 1/233
See application file for complete search history.

(56) References Cited

U.S. PATENT DOCUMENTS

| | | | |
|---|---|---|---|
| 5,025,778 A | 6/1991 | Silverstein et al. | |
| 5,117,818 A | 6/1992 | Palfy | |
| 5,257,617 A | 11/1993 | Takahashi | |
| 5,601,594 A | 2/1997 | Best | |
| 5,879,289 A * | 3/1999 | Yarush | A61B 1/00039 |
| | | | 600/109 |
| 6,091,453 A | 7/2000 | Coan et al. | |
| 6,106,457 A | 8/2000 | Perkins et al. | |
| 6,402,687 B1 | 6/2002 | Ouchi | |
| 6,405,729 B1 | 6/2002 | Thornton | |
| 6,432,046 B1 | 8/2002 | Yarush et al. | |
| 6,750,971 B2 | 6/2004 | Overbeck et al. | |
| 7,559,892 B2 | 7/2009 | Adler et al. | |
| 7,879,061 B2 | 2/2011 | Keith et al. | |
| 8,088,101 B2 | 1/2012 | Chang et al. | |
| 2001/0041825 A1 | 11/2001 | Shibata et al. | |
| 2002/0068851 A1 | 6/2002 | Gravenstein et al. | |
| 2003/0040685 A1 | 2/2003 | Lewkowicz et al. | |
| 2003/0130564 A1 | 7/2003 | Martone et al. | |
| 2004/0027459 A1 | 2/2004 | Segawa et al. | |
| 2004/0092825 A1 | 5/2004 | Madar et al. | |
| 2004/0133089 A1 | 7/2004 | Kilcoyne et al. | |
| 2005/0049462 A1 | 3/2005 | Kanazawa | |
| 2005/0177024 A1 * | 8/2005 | Mackin | A61B 1/00016 |
| | | | 600/120 |
| 2005/0228224 A1 | 10/2005 | Okada et al. | |
| 2006/0137690 A1 | 6/2006 | Gunaratnam et al. | |
| 2006/0206005 A1 | 9/2006 | Ou-Yang et al. | |
| 2006/0235458 A1 | 10/2006 | Belson | |
| 2006/0272640 A1 | 12/2006 | Abullon | |
| 2007/0142703 A1 | 6/2007 | Lu | |
| 2007/0161853 A1 | 7/2007 | Yagi et al. | |
| 2007/0185377 A1 | 8/2007 | Murakami et al. | |
| 2007/0219600 A1 | 9/2007 | Gertner et al. | |
| 2007/0276183 A1 * | 11/2007 | Melder | A61B 1/00011 |
| | | | 600/112 |
| 2008/0021273 A1 | 1/2008 | MacKin | |
| 2008/0103521 A1 | 5/2008 | Makower et al. | |
| 2008/0139881 A1 * | 6/2008 | Cover | A61B 1/00016 |
| | | | 600/103 |
| 2008/0139884 A1 | 6/2008 | Myers | |
| 2008/0232131 A1 * | 9/2008 | Suda | A61B 1/0669 |
| | | | 362/574 |
| 2008/0275483 A1 | 11/2008 | Makower et al. | |
| 2008/0312499 A1 | 12/2008 | Handa et al. | |
| 2009/0095303 A1 | 4/2009 | Sher et al. | |
| 2009/0188507 A1 | 7/2009 | LaCava | |
| 2009/0194109 A1 | 8/2009 | Doshi et al. | |
| 2009/0247828 A1 | 10/2009 | Watanabe et al. | |
| 2009/0253967 A1 | 10/2009 | Gill et al. | |
| 2010/0016673 A1 | 1/2010 | Bandy et al. | |
| 2010/0030031 A1 * | 2/2010 | Goldfarb | A61B 1/00066 |
| | | | 600/163 |
| 2010/0095969 A1 | 4/2010 | Schwartz et al. | |
| 2010/0099946 A1 | 4/2010 | Jenkins et al. | |
| 2010/0100181 A1 | 4/2010 | Makower et al. | |
| 2010/0101580 A1 | 4/2010 | Stumm et al. | |
| 2010/0210901 A1 | 8/2010 | Makower et al. | |
| 2011/0137290 A1 | 6/2011 | Flickinger et al. | |
| 2011/0261183 A1 | 10/2011 | Ma et al. | |
| 2012/0071824 A1 | 3/2012 | Chang et al. | |
| 2013/0204085 A1 | 8/2013 | Alexander et al. | |

OTHER PUBLICATIONS

Aliexpress "Witson New Wifi iPad iPhone Android supported borescope, 9.8mm camera with 2 Leds, Support iPad/iPhone/Android surveilance", http://www.aliexpress.com/store/product/WITSON-NEW-WIFI-iPad-iPhone-aNDROID-SUPP ... [retrieved from the Internet on May 2, 2013], 12 pages.

Euroclinic Medial Equipment, Diagnostic & Imaging. "EVS ED400 Camera System", http:www.euroclinic.it/en/product-php?p=78&d=3, 'retrieved from the Internet on May 2, 2013], 2 pages.

Sanostec, Inc., Sinus Cones vs. Max-Air Nose Cones, Retrieved Nov. 15, 2011 from http://www.maxaimosecones.com/sinus-cones-vs-max-air-nose-cones-products/.gclid=CLrys4--3wsCFYxb7AodiXezQA.

SweetVision Imaging, innovative endoscope imaging systems, http:sweetvision-imaging.com [retrieved from the Internet on May 2, 2013], 10 pages.

* cited by examiner

METHODS OF PERFORMING INTERNAL BODY IMAGING

RELATED APPLICATIONS

This Application claims priority to U.S. provisional patent application Ser. No. 61/548,596 entitled "Nasal Guide and Method of Use Thereof", filed Oct. 18, 2011, and U.S. provisional patent application Ser. No. 61/559,190 entitled "Portable Endoscope and Method of Use Thereof", filed Nov. 14, 2011 and is a continuation of U.S. patent application Ser. No. 13/303,117 entitled "Portable Endoscope and Method of Use Thereof", filed Nov. 22, 2011, all of which are hereby incorporated by reference in their entirety.

BACKGROUND

Each year more and more surgical procedures are performed through the nose. For example, balloon sinuplasty, brain surgery, and cosmetic surgery may be performed through the nose of a patient out of necessity or convenience. In particular, balloon sinuplasty has become more popular in recent years because of enhanced equipment and minimal down time for the patient. Balloon sinuplasty is an endoscopic surgical procedure for the treatment of conditions, such as blocked nasal sinuses. Because the procedure involves the insertion into the nose of balloon catheters, guide wires, and other devices and instruments, such as irrigation catheters, illumination systems, and navigation systems, patients might become uncomfortable and find it difficult to remain still. For example, a physician may insert the sinus guide catheter into a nostril of a patient to gain access to the sinus ostia under endoscopic visualization.

Procedures and surgeries through the nose of the patient require positioning the necessary equipment. Some procedures may require multiple medical professionals to ensure proper guidance and placement of the equipment due to the size and awkwardness of the equipment. In addition, the medical professionals must be careful to prevent unnecessary abrasion of the scope, or other equipment, against the exterior of the nose as well as damaging or irritating the nostrils, nasal passages, and nasal cavity. Current systems, devices, and techniques for performing nasal procedures fail to adequately address these and other issues.

SUMMARY

One embodiment provides a system, method, and wireless endoscope for performing internal imaging. A first portion of a wireless endoscope including at least a lens and a light is connected to a second portion of the wireless endoscope. The first portion is inserted into a body while the second portion remains outside the body. The wireless endoscope is powered on in response to receiving user input from a user. A distal end proximate the lens is illuminated utilizing a light. Video inside the body is captured utilizing a camera in communication with the lens. The video is wirelessly communicated to a receiver associated with a display.

In one embodiment, the first portion is connected with the second portion utilizing a connector. The first portion of the wireless endoscope is configured for insertion into the body and is utilized to visualize nasal cavities.

In one embodiment, a tip of the first portion associated with the lens and the light emitter is diagonally shaped. In one embodiment, the video is communicated in real-time and neither the first portion or the second portion of the wireless endoscope are ingested. In one embodiment, the video is recorded to a memory in response to user input. In one embodiment, the video is formatted for communication to the receiver in response to capturing the video. In one embodiment, the communicating is performed directly between the wireless endoscope and the receiver. In one embodiment, at least the light is controlled utilizing a user interface of the wireless endoscope. In one embodiment, error detection is performed for the video.

In one embodiment, the wireless endoscope includes at least a transceiver and a rechargeable battery.

Yet another embodiment provides an endoscopic system, method, and wireless endoscope for internal imaging. A first portion of the wireless endoscope is received including a lens and a light for connection to a second portion of the wireless endoscope. The first portion is configured for insertion into the body and utilized to visualize internal portions of a body. A rechargeable battery is received for electrical connection to a second portion. The light and a camera are powered on in response to user input. A distal portion proximate the lens is illuminated utilizing the light. Neither the first end nor the second are ingested into the body. The video is captured utilizing a camera in communication with the lens. The video is formatted for wireless communication to the receiver associated with the display device in response to capturing the video. The video is wirelessly communicated from a transceiver of the wireless endoscope to a receiver in communication with a displaying device utilized to display the video.

One embodiment provides a system, method, and portable endoscope. The portable endoscope may include a case configured to enclose at least electrical components of the portable endoscope. The electrical components may include a camera configured to capture video content within a body of a patient. The components may also include one or more lights at least partially encompassing the camera. The one or more lights may be adapted to illuminate internal portions of the body of the patient. The components may also include a transceiver in electrical communication with the camera. The transceiver may be configured to receive the video content from the camera and wirelessly transmit the video content to a computing or communications device. The components may also include a battery configured to provide electrical energy to the camera, the one or more lights, and the transceiver. Each of the electrical components may be interchangeable within the case.

Another embodiment provides an interchangeable endoscope. The interchangeable endoscope may include a case configured to secure components of the interchangeable endoscope. The interchangeable endoscope may also include one or more lights at least partially enclosed by the case. The one or more lights may be adapted to illuminate internal portions of a body of a patient. The interchangeable endoscope may also include a camera positioned adjacent the one or more lights and at least partially enclosed by the case. The camera may be configured to capture video content within the body of the patient. The camera may be interchangeable with one or more additional cameras. The interchangeable endoscope may also include a transceiver in electrical communication with the camera. The transceiver may be configured to receive the video content from the camera and wirelessly transmit the video content to a computing or communications device. The interchangeable endoscope may also include a battery electrically connected to and powering the camera, the one or more lights, and the transceiver.

Yet another embodiment provides a portable endoscope. The portable endoscope may include a camera configured to capture video content with a body of a patient. The portable endoscope may also include one or more lights positioned adjacent the camera. The one or more lights may be adapted to illuminate internal portions of the body of the patient. The portable endoscope may include a case configured to at least partially enclose the camera and the one or more lights. The portable endoscope may include a transceiver external to the case connected to the camera by a cable. The transceiver may be configured to receive the video content from the camera and wirelessly transmit the video content to a computing or communications device. The portable endoscope may include a battery connected to the transceiver and external to the case. The battery may be electrically connected to camera and the one or more lights by the cable to provide power.

In one embodiment, the portable endoscope may be integrated with or include components of a nasal guide.

BRIEF DESCRIPTION OF THE DRAWINGS

Illustrative embodiments of the present invention are described in detail below with reference to the attached drawing figures, which are incorporated by reference herein and wherein.

DETAILED DESCRIPTION OF THE DRAWINGS

Figure 1A:
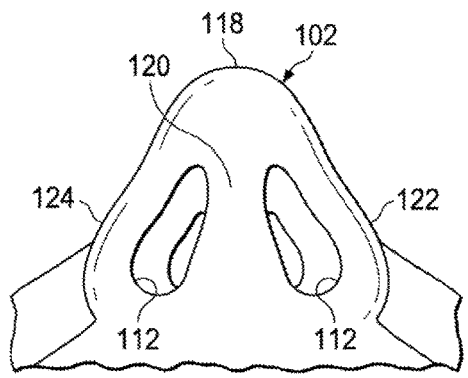
FIGS. 1A-C are pictorial representations of nose and nostril shapes on or in which the illustrative embodiments may be implemented.

Illustrative embodiments provide a nasal guide and a method for utilizing the nasal guide. In one embodiment, the nasal guide provides a guide for inserting one or more endoscopes, catheters, guides, or other pieces of equipment into the nose of a patient for surgery, examination, or other medical procedures. Unless otherwise indicated, as used herein, "or" does not require mutual exclusivity. In particular, the nasal guide directs the medical equipment into the nose of the patient toward the sinuses and stabilizes the equipment during insertion, utilization, and removal of the equipment. As a result, surgeries, such as balloon sinuplasty, may be performed by a single medical professional or fewer medical professionals while still maintaining instrument stability. The nasal guide may include one or more walled openings, lumens, ports, or through-holes for inserting the medical equipment. The lumens may be angled to guide the medical instruments to the sinuses or other interior portion of the body of the patient. The lumens may include stabilization components, such as protrusions that further dampen motion of the medical instruments and stabilize the medical instruments during use whether or not held by the medical professional.

The nasal guide may be configured to be secured utilizing elastic, bands, clips, or adhesives that may be adjusted or customized for each individual patient. For example, an elastic band may include a clip or strings for tightening or loosening the fit of the nasal guide in and against the nose of the patient. The nasal guide may be manufactured in a number of sizes and shapes to fit the noses (including snouts and muzzles) of patients of any age and size including humans and animals. In alternative embodiments, the guide may be configured for a mouth, ear(s), rectum, or other natural or surgically-created opening. In one embodiment, the nasal guide gently expands the nostrils of the patient allowing the equipment and medical professional to more easily access an interior portion of the body or nose including the sinus cavity and sinuses. The opening action of the nasal guide may also help the patient breath before, during, or after the medical procedure is performed.

In one embodiment, the nasal guide may be configured to both receive and guide medical instruments deeper into the nose while expanding the nostrils and stabilizing the medical instruments during the procedure. As a result, fewer medical professionals may be required, and medical procedures may be performed with less concern about damaging the nostrils of the patient. The nasal guide may be configured for use in a single nostril or in both nostrils for enhanced stability. In addition, suction or oxygen attachments may be integrated with, used with, or attached to the nasal guide (portions inserted within the nose as well as external to the nose) to allow suction or oxygen to be applied to the patient through the nasal guide. Any of the components and features of the illustrative embodiments may be combined in a nearly unlimited number of configurations best suited to fit the nose of the patient, the needs of medical professionals, or other purposes.

Another embodiment provides a portable endoscope. In one embodiment, the portable endoscope is a wand-shaped endoscope that may be utilized alone or with the nasal guide. The portable endoscope has a reduced footprint and is self-contained to wirelessly transmit video to one or more computing devices, which may be wired or wireless devices. In another embodiment, the camera of the portable endoscope may communicate and be powered through a wire or cable with an externally-connected transmitter and battery. In one embodiment, the portable endoscope decreases the size and complexity of endoscopic systems and equipment. In addition, the portable endoscope may include interchangeable parts including a camera, lights, processing or logic components, a transmitter or transceiver, and a battery that may be adapted for the patient, medical professional, or medical procedure. Both the portable endoscope and the guide (e.g., nasal guide) may be utilized for any sort of visualization within the body of a patient.

Figure 1B:
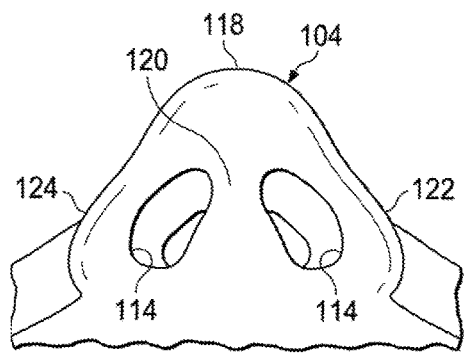
Figure 1C:
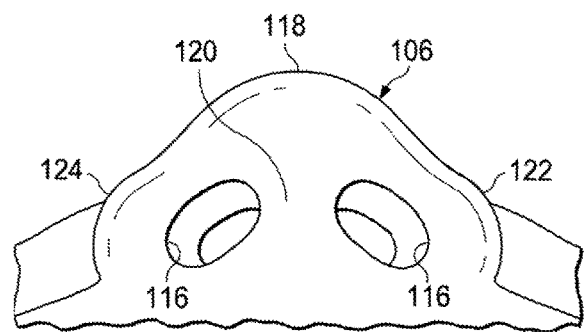

FIGS. 1A, 1B, and 1C are pictorial representations of various noses 102, 104, and 106 and nostril shapes with which the illustrative embodiments may be implemented. The visible part of the nose is the protruding part of the face that bears the nostrils or anterior nares. Typically, the shape of the nose is determined by the ethmoid bone and the nasal septum. The nasal septum separates the left and right airways of the nose to divide the two nostrils, and is formed mostly of cartilage. Nose and nostril sizes, shapes, and configurations vary by age, sex, race, and other factors. In addition, accidents, birth defects, and other factors may influence the size and shape of interior and exterior portions of the nose, and such circumstances may be accounted for by the illustrative embodiments.

The nostrils 112, 114, and 116 vary between the different noses 102, 104, and 106. As shown for nose 102, the nose 102 includes a tip 118, columella 120, left lateral side 122, and right lateral side 124. The nasal guides of the illustrative embodiments are sized and shaped to conform to any number of noses and nostrils despite the differences in size and shape. The nasal guides may be utilized to guard against abrasion or damage to the nostrils 112, 114, and 116, and the interior and exterior periphery of the nose about the nostrils 112, 114, and 116 including the columella 120.

In one embodiment of the nasal guide, and use thereof, the patient may be distracted by the tactile sensation of the portion of the nasal guide that fits into the patient's nostril(s) instead of focusing on the actual medical procedure that is being performed. As a result, scopes and other medical instruments may be more easily inserted and removed from the nostrils without damaging the soft interior and exterior skin and tissues of the nose.

In the illustrative embodiments, the term "patient" is utilized to refer to any individual, user, or animal that may have a medical procedure or other process performed through the nostrils of the nose, snout, or muzzle, or other natural or surgical opening of the body. Although the noses 102, 104, and 106 shown are human noses, the nasal guides may be sized and configured to be utilized for any patient, including any human, animal, or living creature. Non-limiting examples of animals on which the nasal guide may be used include domestic and exotic animals (i.e., mammals, reptiles, amphibians, marsupials, etc) of all sizes from cows and zebras to dogs and ferrets. The term "medical professional(s)" is utilized to refer to any doctor, professional assistant, nurse, dentist, veterinarian, remote operating system and device, clinician, forensic analyst, pathologist, diener, robot, or other person or electronic device that may perform a medical procedure or other process on a patient. It will be appreciated that operation of the nasal guide is not limited to medical professionals, as, in one embodiment, a user may self-administer, position, or self-install the nasal guide, as well as any associated medical or other procedures.

Figure 2:
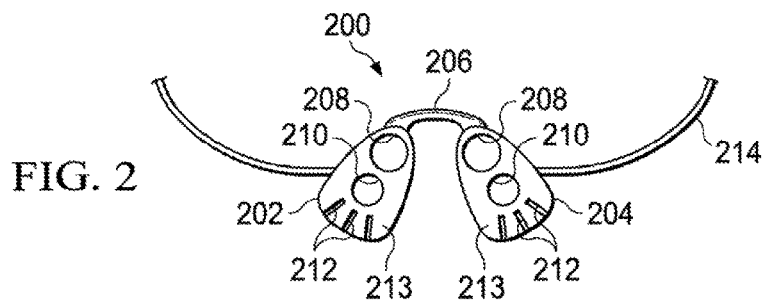
FIG. 2 is a schematic, plan view of a nasal guide in accordance with an illustrative embodiment.

FIG. 2 is a schematic, pictorial representation of a nasal guide 200 in accordance with an illustrative embodiment. The nasal guides of FIGS. 2-6 are shown from a plan view from which the nasal guides 200, 300, 400, 500 may be adjusted and fit into noses of any patients, such as the noses 102, 104, and 106 of FIGS. 1A, 1B, and 1C. The nasal guide 200 may include any number of components or elements as herein described. The potential size and shape of the nasal guide 200 are as varied as the patients that the nasal guide 200 may be used on.

The nasal guide 200 may alternatively be a guide for any body orifice or opening (e.g., ear, mouth, rectum, etc.), passageway, or tissue plane naturally or surgically created. For example, the guide may be adapted for use with an endoscope (such as the one subsequently described) for laparoscopic abdominal surgery, orthopedic procedures, robotic surgery, or intracranial or ear surgery. The nasal guide 200 may be used when numerous medical instruments are inserted into the body. The exterior portion (i.e., the portion of the guide adapted to be outside of the body) and the interior portion (i.e., the portion of the guide adapted to be inside of the body) of the guide may be configured for the surrounding entry site whether it be the ear or rectum of the patient, a surgically-created opening through the belly button of the patient, or other openings. For example, the exterior portion of the guide may be substantially flattened to be fit to the patient. In addition, the guide may have only one side, or support, instead of two (e.g. the potential two-sided configuration of the nasal guide 200, shown in FIG. 2, may be for use in both nostrils).

In one illustrative embodiment, the nasal guide 200 is formed from hypoallergenic medical grade materials, such as U.S. Pharmacopeia (USP) Class V and VI silicon, rubber, polymers, or plastic materials (or a combination thereof), including those known in the art. In one embodiment, the nasal guide 200 is clear or transparent to provide the medical professional with maximum visibility of all covered and uncovered portions of the nose, whether exterior or interior to the nostrils. In one example, the nasal guide may be molded from a single piece of medical grade plastic, silicon, composite, or rubber. Alternatively, multiple components of different materials may be connected or fused together. In one embodiment, the plastic is see-through, translucent, or transparent to provide the medical professional additional visibility of all portions of the nose of the patient. As a result, a light source may be connected to the nasal guide 200 so that it may act as a light guide.

In one embodiment, before use or application of the nasal guide 200, the shape of the nasal guide 200 may be molded or fit to a mold or nose of the patient. For example, the nasal guide 200 may be heated in hot water and then formed to the size and shape of the nose of the patient. A separate insulating layer or surface may coat or be attached the portion of the nasal guide 200 contact the skin, tissue, and cartilage of the patient to prevent burning the patient during the molding process. The insulating layer may also have medicinal properties as herein described. In another embodiment, one or more pictures, a three-dimensional image, x-ray, MRI, or other scan of the nose may be utilized to create or mold the nasal guide 200. For example, an image may be utilized by an injection molding system to create the nasal guide 200. In yet another example, the nasal guide 200 may be adjusted manually using the flexible material properties of the components of the nasal guide 200.

The nasal guide 200 may also have anti-fungal, anticoagulant, procoagulant, and/or anti-bacterial properties for preventing the spread of infections from the mouth or lips to the inside of the nose and brain. In one embodiment, the material of the nasal guide 200 may be formulated, molded, impregnated, injected, coated, or otherwise created with any of the described compounds, materials, or properties to prevent any unwanted spread of germs or infection. For example, the nasal guide 200 or an interior portion of the nasal guide 200 inserted into the nose may be coated with an anesthetic agent, such as lidocaine cream to make the nasal guide 200 more comfortable.

In one embodiment, the nasal guide 200 includes a left support 202, a right support 204, a bridge 206, upper lumens 208, lower lumens 210, drains 212, and an elastic 214. In one embodiment, the left support 202 and right support 204 (collectively the "supports") are the supportive framework of the nasal guide 200 that prevents the nasal guide 200 from slipping into the nostrils, and in which the lumens 208, 210 are formed. The supports 202 and 204 may help prevent the nasal guide 200 from slipping during a medical procedure. The supports 202 and 204 may also guard covered portions of the nose from contact with objects, such as medical instrumentation. The left support 202 and right support 204 are each configured to abut, be placed against, adjacent, or proximate left and right portions of the nose and nostrils, respectively. The supports 202 and 204 may also be placed in contact with the columella, philtrum, and upper lip. In one embodiment, the supports 202 and 204 are directly coupled to one another for additional support without the need for a bridge 206.

Figure 3:
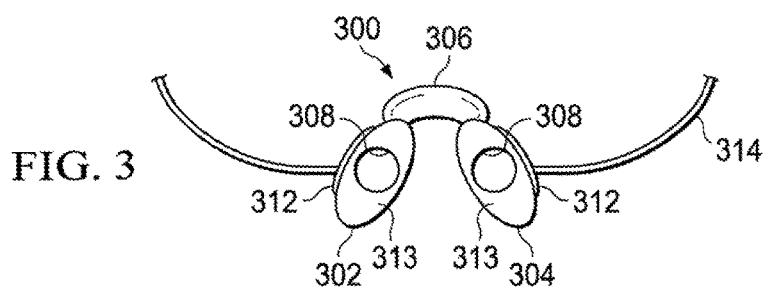
FIG. 3 is a schematic, plan view of another nasal guide in accordance with an illustrative embodiment.

In one embodiment, the supports 202 and 204 may include lateral edges or extensions (not shown) that extend perpendicular to the general plane 213 of the supports 202 and 204 on the outer edges of the supports 202 and 204 for cradling the sides of the nose of the patient during use of the nasal guide 200 (see the lateral edges 312 of FIG. 3 for an example). The supports 202 and 204 may also extend or include extensions to be supported by the cheeks of the patient. For example, in an embodiment of the nasal guide 200 that may be appropriate for intensive surgeries, the supports 202 and 204 may be shaped to extend out to and be braced or flattened against the cheeks of the patient. In one embodiment, the lateral edges (see, e.g., FIG. 3) stabilize the nasal guide 200 as medical instruments are inserted into and removed through the upper lumens 208 and lower lumens 210. For example, the lateral edges may provide lateral stability. The lateral edges are further shown and described in FIGS. 3 and 7-10.

With reference to FIG. 3, the lateral edges 312 may act, and be shaped, as clips for gently securing the nasal guide 300 against the sides of the nostrils during utilization of the nasal guide 300. The lateral edges 312 may be wide enough to secure an entire or substantial portion of the side of the nostril when the nasal guide 300 is attached.

Referring again to FIG. 2, in one embodiment, the nasal guide 200 may include the bridge 206, which may be a connector or other element between the supports 202 and 204. The bridge 206 may be configured so that the angle and position of the left support 202 and right support 204 may be adjusted to fit the size and shape of the nose and nostrils of the patient. The bridge 206 itself and the connection points between the bridge 206 and supports 202 and 204 may be flexible, allowing the nasal guide 200 to be positioned, flexed, or stretched as needed for the patient's nose or medical procedure. This allows the nasal guide 200 to be contoured, or otherwise fitted, to different sized and shaped noses and nostrils. As shown in the various embodiments, the bridge 206 may be placed at, or connected to, the top, middle, or bottom of the supports 202 and 204 or lateral edges or at any position therebetween.

In another embodiment, the nasal guide 200 may include multiple bridges for connecting the supports 202 and 204. For example, bridges may be attached to the top and bottom of the left support 202 and right support 204 curving in the same or different directions (e.g., curving up and down respectively) to allow the bridges to be flexed or stretched as needed to fit the nose of a patient. The bridge 206 or bridges may be connected to the inside or outside edges, top, bottom, or middle of the supports 202 and 204.

In one embodiment, the bridge 206 is positioned between the supports 202 and 204 and attaches to the middle of the supports 202 and 204 on the inside edges to provide maximum flexibility for moving the supports 202 and 204 toward each other and adjusting the angle of the supports to conform to the nostrils. In another embodiment, the nasal guide 200 may not include a bridge 206 and instead the supports 202 and 204 may be directly or flexibly connected to one another. The bridge 206 may be a cylindrically-shaped, rounded, or flattened connector for providing comfort or support when freely positioned away from the nose or positioned against the columella, tip, bridge, or other portion of the nose.

The upper lumens 208 and lower lumens 210 (collectively the "lumens") are tubes or other passageways including openings through which the medical instruments may be inserted or communicated. Alternatively, the lumens 208 and 210 may be referred to as openings, through-holes, or guides. The lumens 208 and 210 may be formed by or in the supports 202 and 204, and may be defined by walls that extend beyond the plane of the supports 202 and 204 such that passageways into the nostrils are provided. In one embodiment, the lumens 208 and 210 may extend substantially perpendicular from the general plane 213 of the supports 202 and 204. However, the lumens 208 and 210 may also be angled relative to the general plane 213 of the supports 202 and 204.

In another embodiment, the walls of the lumens 208 and 210 may be short and extend inward and toward the bottom of the nasal cavity or passage for applying suction within the nose. For example, an interior end of the lumens 208 and 210 may have a tapered end, or open in a scoop or funnel shape for applying suction. In yet another embodiment, the walls of the lumens 208 and 210 may extend or curve slightly upward or to a side from the supports 202 and 204 to better guide medical instruments toward a specific sinus in the nasal cavity. In one embodiment, the nasal guide 200, and particularly the lumens 208 and 210, may be configured to be inserted anywhere from 0-10 centimeters (e.g., 2-10 cm) or more into the nose of the patient. In another embodiment, the nasal guide 200, and particularly the lumens 208 and 210, may not enter the nostrils at all, and instead may be positioned near the opening of the nostrils or extend externally from the nasal guide 200.

The lumens 208 and 210, including the walls thereof, may protrude past the general plane 213 of the supports 202 and 204 to both guide and stabilize medical instruments. In some cases, longer lumens 208 and 210 may simplify performing medical procedures without additional endoscopes, catheters, or instruments. For example, a greater length of the lumens 208 and 210 may better stabilize a portion of the medical instruments inserted through and positioned in the lumens 208 and 210. In one embodiment, either end of the lumens 208 and 210 may be configured to receive inwardly extending or externally protruding extensions. The extensions may be straight or curved or have any of the other properties described for the nasal guide 200 and lumens 208 and 210.

The diameter of the lumens 208 and 210 may vary based on the application. In one embodiment, the opening of the lumens 208 and 210 are between 5 mm-2.5 cm in diameter for human applications, but this may vary. In one embodiment, the size or diameter of the lumens 208 and 210 may be uniform along the length of the nasal guide. In another embodiment, the size of the lumens 208 and 210 may narrow slightly at the interior end allowing the nasal guide 200 to have a more conical or funnel shape for easy insertion of medical instruments. Additionally, the conical or funnel shape may naturally expand the nostrils when inserted.

Also, in one embodiment, any of the openings of the lumens 208 and 210 may be flared so that medical instruments do not catch on internal or external (to the nose) edges of the lumens 208 and 210.

The lumens 208 and 210 may utilize any number of symmetrical or asymmetrical shapes, such as circles, ellipses, polygons, tear drop shapes, etc. The walls may similarly define these shapes extending from the supports 202 and 204. In another embodiment, the lumens 208 and 210 and corresponding walls may form a cylindrical, conical, or hyperbolic shape extending into the patient's nasal cavities when the nasal guide 200 is inserted as shown in FIGS. 6-10. In one embodiment, both ends of the lumens 208 and 210 may be flared and rounded to prevent medical instruments from catching on the openings as medical instruments are inserted and removed from the nose of the patient. In one embodiment, the openings of the lumens 208 and 210 may be at least partially covered with a flexible material with one or more slits, slots, notches, or perforations (e.g. forming a diaphragm or membrane with an opening) for sliding the medical instruments in and out. For example, the openings of the lumens 208 and 210 may be shaped similar to the portion of the lid of a cup adapted to receive a straw. The slits may support the medical instruments and prevent the spread of fluids or leakage of fluids.

In one embodiment, the lower lumens 210 may be positioned lower on the supports 202 and 204 for use in applying suction through the nasal guide 200. The lower lumens 210 may be closer to the bottom of the nostril and more proximate the lip of the patient when the nasal guide 200 is positioned on the patient. For example, during a medical procedure, mucus, blood, or other fluids may pool against the supports 202 and 204 of the nasal guide 200. The lower lumens 210 may be positioned to suction out these fluids. In one embodiment, the lower lumens 210 may be short to allow the fluids to flow out of the nasal guide 200 through the lower lumens 210. In another embodiment, inwardly-extending walls of the lower lumens 210 may extend straight or at an angle to be proximate or touch a bottom portion of the nasal cavity where fluids are most likely to collect. The inwardly-extending walls may also extend at an angle to a general plane 213 of the supports 202 and 204.

In another embodiment, one or both of the lumens 208 and 210 may also extend outwardly from the nostrils and define ports for applying or attaching specially-made or traditional oxygen or suction fittings, adapters, systems, or devices, such as an oxygen system (e.g. through a nasal cannula), or tubes. Alternatively, the interior or exterior portions of the lumens 208 and 210 may be configured to receive adapters (now shown) for providing suction or oxygen through the nasal guide 200 or extending the reach or direction of the lumens 208 and 210. The shape and configuration of the adapters may also vary. For example, the adapters may be funnel shaped for receiving medical instruments. Alternatively, the adapter may include a 90° bend for reaching a particular sinus.

In one embodiment, the adapters may be inserted into the lumens 208 and 210 and may remain in place due to tight tolerances and friction between the lumens 208 and 210 and adapters. In another embodiment, the lumens 208 and 210 and adapter may include threads, barbed connectors, or locking tabs allowing the adapter to be screwed or snapped into the nasal guide 200. For example, immediately after a medical procedure is performed, oxygen and/or suction may be attached to the nasal guide 200 without using other instruments. As a result, time and resources may be saved without further inconveniencing the patient by adding and removing additional components. The lumens 208 and 210 may then act as nozzles for delivering oxygen or for coupling suction ends to apply suction to the nasal cavity of the patient. Oxygen or suction may also be applied to the lumens 208 or 210 during a medical procedure as needed. For example, the oxygen may be applied during the procedure to keep the interior of the nose dryer. In one embodiment, the interior end of the lumens 210 may be formed in the shape of a scoop that fits within the nasal passage to channel any blood, mucous, or fluids through the lumens 210 for removal. The scoop end of the openings on the internal side of the nasal guide may be wide enough to fit along the entire width of the bottom and sides of the nasal passage to channel the fluids through the lumens 210.

In one embodiment, the lumens 208 and 210 may not extend past the general plane 213 of the supports 202 and 204. Instead, the lumens 208 and 210 may extend away from the nose and nostrils of the patient when positioned on the patient. As a result, the lumens 208 and 210 may not irritate the patient's nasal cavity. Exterior lumens may similarly stabilize and guide medical instruments to the correct position. Alternatively, a combination of internally and externally lumens 208 and 210 may be utilized. For example, the nasal guide 200 may include additional guides, rings, or other supports for supporting a portable endoscope as is subsequently described. In one embodiment, the lumens 208 and 210 may be dilated, collapse, or include a circularly-folding structure for adjusting the diameter of each lumen. As a result, the size of the lumens 208 and 210, or other components of the nasal guide 200 may be adjusted or customized for the patient.

In another embodiment, the nasal guide 200, the supports 202 and 204, the lumens 206 and 208 may be cut down or sized to fit the patient. In one embodiment, the nasal guide 200 may include perforations (or thinner or weaker areas) for cutting or breaking away sections of any portion of the nasal guide for customization for the patient. The nasal guide 200 may also include markings, such as metric or English unit measurements, for properly sizing and utilizing the nasal guide 200. Such markings may be inscribed, molded, etched, printed, or otherwise included on the nasal guide 200.

In one embodiment, the nasal guide 200 may include drains 212. The drains 212 are one or more openings, slits, or notches through a portion of the nasal guide that allows fluid to pass through, below, or around the nasal guide 200. The drains 212 may allow fluids to bypass the nasal guide 200 to be dealt with in any number of ways. The drains 212 may utilize any number of shapes or configurations. In one embodiment, the drains 212 may be semi-circular, rectangular, or square shaped. In another embodiment, the drains 212 may be a single cut-away portion of the supports 202 and 204 allowing the fluids to flow under the supports 202 and 204. For example, the fluids may be soaked up by gauze or suctioned by the medical professional once past the supports 202 and 204 of the nasal guide 200.

In one embodiment, the supports 202 and 204 may include a clip, or other attachment mechanism, for attaching gauze in such a way that the gauze absorbs the fluid that passes through the drains 212 without interfering with insertion or removal of medical instruments through the lumens 208 and 210. The clip may also be utilized to attach the end of a suction device. The clip may extend from any surface or edge of the supports 202 and 204.

The nasal guide 200 may include headgear or other securing component(s), device(s), or mechanism(s). In one embodiment, the headgear is the elastic 214. The elastic 214 is a fastener usable to secure or stabilize the nasal guide 200 during use. In one embodiment, the elastic 214 is an elastomer or other stretchable material that may be utilized to secure the nasal guide 200 about the head, ears, personal or medical accessories (i.e. glasses), or neck of the patient. The elastic 214 may attach to the supports 202 and 204 or the lateral edges of the supports 202 and 204. The elastic 214 may be one or more narrow or wide bands. The wider band may provide additional surface area and more comfort to the user. For example, the elastic 214 may be neoprene straps that are secured around the neck or head of the patient utilizing a hook and loop strap, barbed connector, Velcro, buckle, or other known securing mechanism on either end of the neoprene straps. In one embodiment, the headgear may be attached to and removed from the nasal guide for repeated use. The headgear may be configured to be washed or otherwise sanitized as needed.

In one embodiment, the elastic 214 is formed of or covered by a cloth material for the comfort of the patient. The elastic 214 may have a high elastaine content for adjusting to the size and shape of the applicable portion of the patient (e.g., head, neck, or ears), including adults or children. As with other elastics, a portion of the elastic 214 may be pulled through holes (not shown) of the supports 202 and 204 (or lateral edges of the supports 202 and 204) to tighten the fit of the nasal guide 200 when worn by the patient. Alternatively, a belt strap-type configuration may be utilized for the elastic 214. Any number of adjustment mechanisms or components may be utilized with the elastic 214 or other securing mechanism to properly fit the nasal guide 200 to the patient. Skin glue, tape, or other similar components may be utilized in a stand-alone configuration or with the elastic 214 to secure the nasal guide 200.

In one embodiment, the nasal guide 200 may include a single support, such as the support 202, and no bridge 206. The elastic 214 may be attached to either or both sides of the support 202 and may be used for situations where the medical professional(s) only needs access through the nostril on one side of the nose, or any single opening on the patient's body. Alternatively, the nasal guide 200 may be moved between nostrils to save materials and expense of manufacturing. In one embodiment, the nasal guide 200 may be used a single time before being disposed. The nasal guide 200 may also be configured for repeated use, including repeated use after sterilization. For example, the nasal guide 200 may be run through and sanitized by an autoclave without being ruined or altered. The single support size of the guide may also be utilized for other natural or surgically-created orifices or body parts. For example, the support 202 may conform to the shape of an ear, buttocks, incision in the abdomen, and so forth.

In one embodiment, the nasal guide 200 may include differently-sized or shaped supports 202 and 204 that may be linked by the bridge 206 such that the support 202 has a different size or shape than the support 204. For example, a patient with an irregular nose or nasal valve collapse may require that the supports 202 and 204 and/or lumens 208 and 210 are differently-sized or shaped for each size or shape of the nose. In one embodiment, the bridge 206 or supports 202 and 204 may be separately created (e.g. molded), clipped, or otherwise attached to one another to be customized for the patient.

In another embodiment, the supports 202 and 204, lumens 208 and 210 (whether single openings or multiple openings are utilized), and corresponding framework or walls may be referred to as nozzles.

In another embodiment, the nasal guide 200 may include interchangeable components that allow a medical professional to customize or assemble the nasal guide 200 for each patient. For example, the supports 202 and 204 and bridge 206 may be the framework or support structure of the nasal guide 200 that may be selected. The supports 202 and 204 may be configured to receive a lumen module (not shown). The lumen module is a fitting adapted to be connected to each of the supports and includes one or more lumens. In one embodiment, the lumen module may be conically shaped for expanding each nostril as is described herein. In one example, the lumen module may include three 2 mm lumens for receiving multiple instruments. The number of lumens 208 and 210 utilized in the nasal guide 200 is not limited, but may be between 1 and 6. In another example, the lumen module may include one 8 mm lumen or two 4 mm lumens. The lumen module may be attached or removed from each of the supports 202 and 204. As a result, the nasal guide 200 may be utilized repeatedly by assembling the distinct parts for each patient. In one embodiment, the medical professional may include various sizes and configurations for each of the components of the nasal guide 200 for adapting the nasal guide 200 for each individual patient and medical procedure.

FIG. 3 is a schematic, pictorial representation of a nasal guide 300 in accordance with another illustrative embodiment. The nasal guide 300 of FIG. 3 may include a left support 302, a right support 304, bridge 306, lumens 308, lateral edges 312, and an elastic 314.

In this embodiment, the supports 302 and 304 are oval shaped to more closely fit the size and shape of certain nostrils and noses. For example, the supports 302 and 304 may be positioned to abut against the bottom portion of the noses with the lumens 308 extending into the nostrils and toward the nasal cavities. As shown in FIG. 3, each of the supports 302 and 304 forms a respective lumen 308 for receiving one or more medical instruments. In one embodiment, the lumens 308 are larger for receiving a larger single instrument or multiple instruments at once.

In the nasal guide 300, the bridge 306 may be shaped differently for various functions. In this embodiment, the bridge 306 is configured to support, surround, or cup the tip of the nose of the patient. For example, the bridge 306 may be shaped to extend along the bottom of the nose of the patient with a portion of the bridge 306 being substantially rounded or bent to conform to the typical rounded shape of the tip of the patient's nose.

The nasal guide 300 may also include lateral edges 312. The lateral edges 312 are stabilizers configured to support or abut the lateral, or side, edges of the nose to provide external alignment with the nostrils. The lateral edges 312 may extend substantially perpendicularly from the surface or general plane 313 of the supports 302 and 304, and may also extend toward the face of the patient when the nasal guide 300 is in use. The lateral edges 312 may further stabilize the nasal guide 300 during use and performance of a medical procedure. In one embodiment, the lateral edges 312 may be elongated semicircles. In another embodiment, the lateral edges 312 may be small arms, tabs, clips, or extensions that are shaped as a square, rectangular, or elliptical. The lateral edges 312 and other portions of the nasal guide 300 may be padded or include an additional material to make the nasal guide 300 more comfortable when positioned against the skin.

In one embodiment, the lateral edges 312 may help secure the nasal guide by holding, or abutting against, both the interior and exterior of the nose. For example, the lateral edges 312 and walls of the opening or lumen may act as a clip securing the nasal guide 300 to the inside and outside of the edges of the nostrils.

Figure 4:
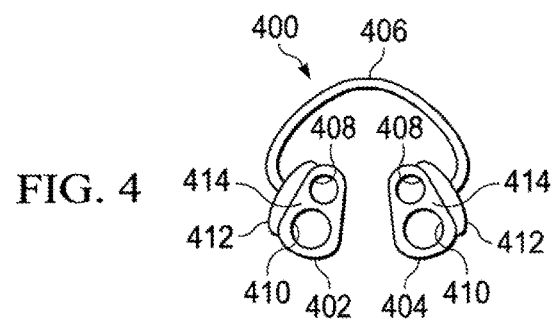
FIG. 4 is a schematic, plan view of another nasal guide in accordance with an illustrative embodiment.

FIG. 4 is a schematic, plan view of a nasal guide 400 in accordance with another illustrative embodiment. The nasal guide 400 includes upper lumens 408 and lower lumens 410 that are differently sized for receiving medical instruments. The size and shape of the upper lumens 408 and lower lumens 410 may depend on the type of medical procedure being performed and the medical instruments involved. The upper lumens 408 and the lower lumens 410 may be positioned horizontally (side-by-side), diagonally, or in any other position with respect to one another.

The nasal guide 400 includes a bridge 406 that is also configured as a clip. The bridge 406 may be biased to push the supports 402 and 404 toward each other and secure the nasal guide 400 on, within, and to the nose of the patient. In another embodiment, the bridge 406 may be biased to push the supports 402 and 404 away from each other to further expand the nostrils of the patient while still securing the nasal guide 400. The bridge 406 may secure the nasal guide 400 without the need for elastic or other securing mechanisms. The bridge 406 may be integrated with or attach to lateral edges 412 or directly to the supports 402 and 404. In one embodiment, the bridge 406 extends directly upward in line with or parallel to the general plane 414 of the supports 402 and 404. The bridge 406 may also be angled such that the top of the bridge 406 extends in front of or behind the supports 402 and 404. In another embodiment, the bridge 406 may connect to the lateral edges 412 and extend away from the general plane 414 of the supports 402 and 404 above the bridge of the nose.

In one embodiment, the bridge 406 may be sized and shaped such that the bridge 406 does not touch the nose of the patient. In another embodiment, the bridge 406 may abut the outside edge of the nose of the patient to provide another point of contact for stabilizing the nasal guide 400. In one embodiment, the bridge 406 may include a shield, or blinders, clips, or attachments for such components, to prevent the patient from seeing the insertion and removal of the medical instruments. For nervous, fearful, or scared patients that are awake, blocking the sight of the patient may help the patient to not focus on what may be seen. In addition, the tactile sensation of the nasal guide 400 may help the patient not focus on the medical procedure being performed. The interior and exterior of the nose includes a large number of nerves. The sensation of the nasal guide 400 being inserted and worn may distract the patient from more significant pain or sensations that results from performance of the medical procedure.

Figure 5:
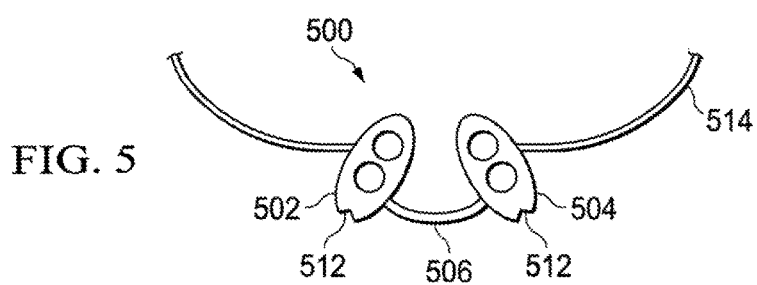
FIG. 5 is a schematic, plan view of another nasal guide in accordance with an illustrative embodiment.

FIG. 5 is a schematic, pictorial representation of a nasal guide 500 in accordance with another illustrative embodiment. The nasal guide 500 further illustrates a bridge 506 positioned at a middle or bottom portion of the supports 502 and 504. The positioning and interconnection of the bridge 506 and elastic 514 may be configured to best fit different sizes and shapes of noses. Drains 512 may be shaped as a single opening for allowing the fluid to flow past the supports 502 and 504. For example, the drains 512 may be rounded in the form of a semi-circle for the comfort of the user.

Figure 6:
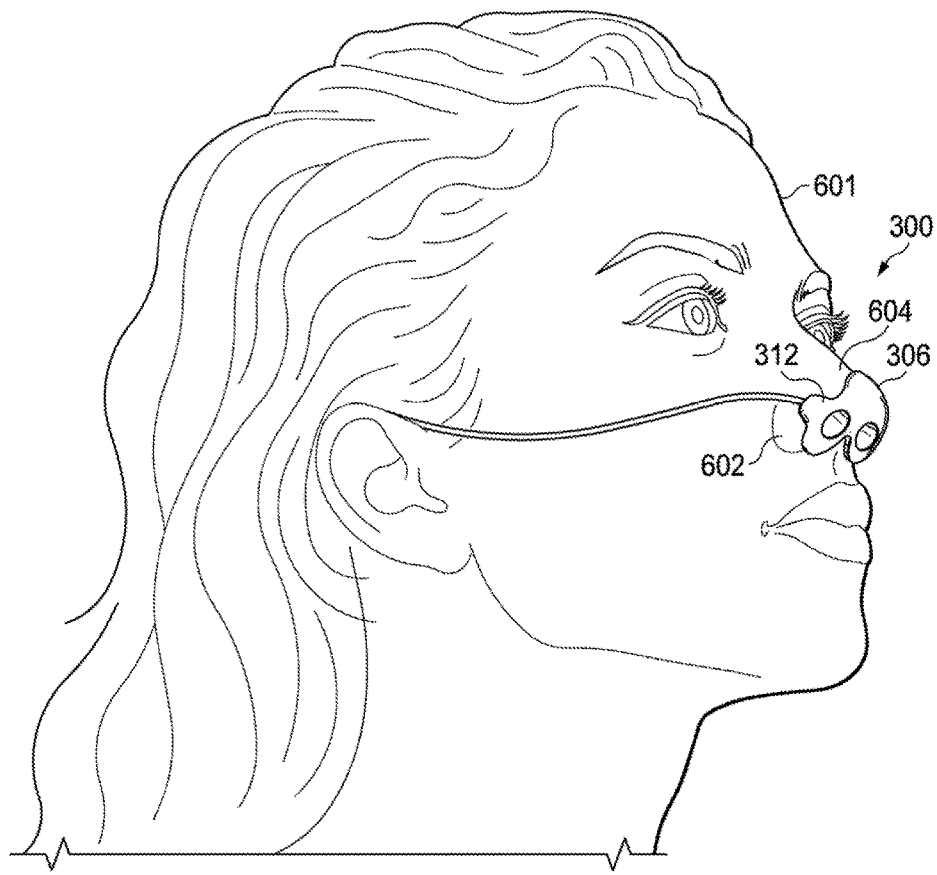
FIG. 6 is a schematic, pictorial representation of a nasal guide installed on a patient in accordance with an illustrative embodiment.

FIG. 6 is a perspective pictorial representation of the nasal guide 300 of FIG. 3 applied to a patient 601 in accordance with an illustrative embodiment. The nasal guide 300 of FIG. 6 illustrates utilization of the nasal guide 300 on a nose 602 of a patient 601. The lateral edges 312 wrap around the edge of the nose 602 to further secure the nasal guide 300 from horizontal motion during the medical procedure.

The bridge 306 may cup or support the tip of the nose 602 to provide vertical and/or horizontal support. The bridge 306 may also wrap around the entire tip of the nose 602 to further secure the nasal guide 300 from vertical motion during the medical procedure. In other embodiments, the bridge 306 may be flattened or rounded to abut against the bottom of the nose 602 when the nasal guide 300 is positioned or installed. In yet another embodiment, the bridge 306 may extend back or up from the supports 302 and 304 toward the eyes of the patient 601. In such a configuration, the nasal guide 300 may sit along a top 604 or bridge of the nose 602.

Figure 7:
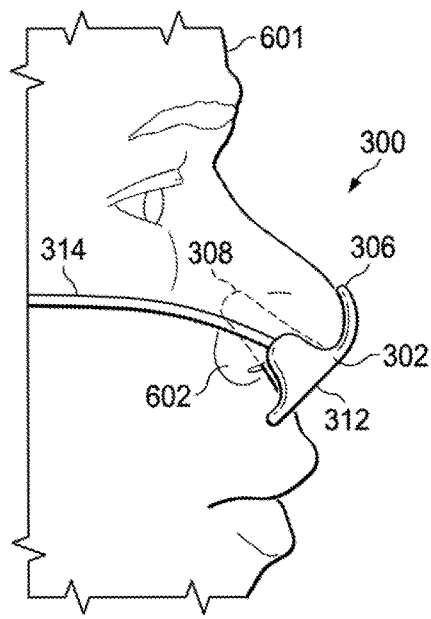
FIG. 7 is a schematic, side-view of a nasal guide in accordance with an illustrative embodiment.

FIG. 7 is a schematic, side view of the nasal guide 300 of FIG. 3 in accordance with an illustrative embodiment. FIG. 7 further illustrates a potential shape and configuration of the nasal guide 300 for adding additional horizontal and vertical stability. The support 302, bridge 306, and lateral edge 312 stabilize the nasal guide 300 vertically and horizontally. In addition, the lumens 308 are shaped to extend inward from the supports 302 and 304. Although a second support is not shown, the nasal guide 300 may include both supports 302 and 304 (described above) from which the lumens 308 extend.

In one embodiment, the lumen 308 is conically-shaped and extends into the nasal cavity of the patient 601 during use. The cone or wedge shape of the lumens 308 that extends from the openings in the supports 302 and 304 may be useful for naturally expanding the nostrils of the patient 601 as the nasal guide 300 is inserted and the pulled towards the face of the patient 601 by the elastic 314. The cone shape of the lumens 308 facilitates natural expansion of the nostrils without causing pain for the patient 601. As a result, the medical instruments may be more easily inserted and removed from the nose 602. The lumens 308 may include a solid surface ensuring that medical instruments do not catch or snag during insertion or extraction through the nasal guide 300. In another embodiment, the lumens 308 may have a spaced surface for saving material. For example, a honeycomb or triangular support framework may support or constitute the one or more lumens 308 that are part of the nasal guide 300.

In one embodiment, the lumens 308 may curve slightly upward to better guide medical instruments to the sinuses and nasal cavity. For example, the supports 302 and 304 may sit flat against the bottom of the nostrils and the curved shape of the lumens 308 may better guide medical instruments. In one embodiment, the interior surface of the lumens 308 may also include ridges (not shown) that run parallel to the nasal cavity for better guiding the medical instruments. The ridges may be flexible for providing additional support to the medical instruments while still allowing the medical instruments to be maneuvered and moved as needed. In another embodiment, the interior portion of the lumens 308 may include flexible extensions, protuberances, or arms (not shown) that further stabilize the medical instruments while providing a small amount of friction or tactile feedback to the medical professional. The flexible protuberances are configured to give way and bend when the medical professional moves the medical instruments, but also provide support while the medical instruments are in use. The flexibility, diameter, length, proximity, and number of protuberances may vary based on the amount of resistance that is desired. As a result, motion of the medical instruments may be slightly opposed to provide enhanced stability and smoothness to the movements of the medical instruments. The lumens 308 may also include rifling or narrowing segments. The lumens 308 may also include notches, threads, or ridges that may correspond to the medical instrumentation being utilized ensuring that the medical instrumentation enters in a proper alignment and is secured during utilization.

The lumens 308 may utilize a conical shape formed from a solid or substantially non-spaced material; such lumens 308 prevent the medical instruments from catching on the lumens 308 when inserted and removed from the nasal guide 300. The ends of the lumens 308 at the interior and exterior openings may flare outward so that the medical instruments do not catch on the edges of the lumens 308 during use. Alternatively, the lumens 308 and other portions of the nasal guide 316 may include cut-outs or integrated spaces for conserving the material utilized to form the nasal guide 300 when molded or assembled. The spaces may also provide additional flexibility to all or portions of the nasal guide 300. As a result, the nasal guide 300 may be deformed while being positioned on the patient 601 to best fit the nose 602 of the patient 601.

In one embodiment, the nasal guide 300 may be injection molded from a single piece of material in default or custom sizes and configurations. For example, the openings and overall size of the nasal guide 300 may be created to specifically fit the nose 602 of the patient 601 based on a picture or scan. The picture or scan may be digitized and utilized to properly size the nasal guide 300. In another embodiment, the different portions of the nasal guide 300 may be formed from different materials. For example, the lateral edges 312 may be formed of a more flexible material (e.g., plastic, latex, etc.) for adjusting to the size and shape of the nose 602 of the patient 601. The bridge 306 may be formed of a stiffer form of plastic for providing additional support.

Figure 8:
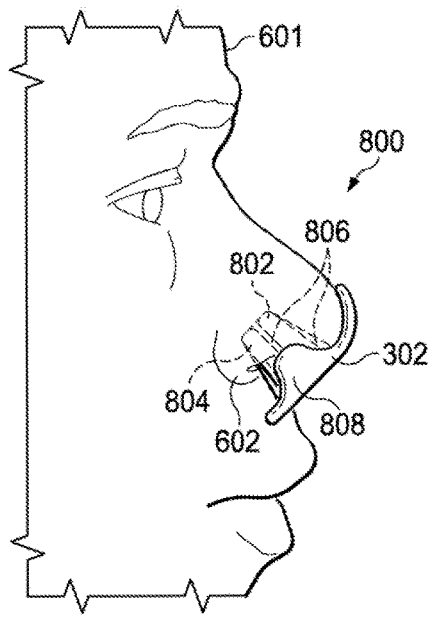
FIG. 8 is a schematic, side-view of another nasal guide in accordance with an illustrative embodiment.

FIG. 8 is a schematic, side-view of a nasal guide 800 in accordance with another illustrative embodiment. The nasal guide 800 includes multiple lumens 802 and 804 instead of a single opening instead of a single lumen. The nasal guide 800 may include additional supports or walls 806 between the lumens 802 and 804 and the supports 302 (and 304 not shown) of the nasal guide 800. The framework of the nasal guide 300, including the additional supports 806, may prevent deformation of the nasal guide 800 and the lumens 802 and 804 during insertion and removal of medical instruments. For example, the additional supports 806 may provide a framework enclosing the lumens 802 and 804 within a conical shape. In another embodiment, the supports 806 may enclose the lumens 802 and 804 with a cylindrical shape. The nasal guide 800 may clip to the nostrils of the nose 602 of the patient 601 with the lateral edges of the nostrils being secured between the lateral edges 808 and the supports 806 (or alternatively between the lateral edges 808 and the lumens 802 and 804). In another embodiment, the lumens 802 and 804 (or any of the other lumen or adapter configurations herein described) may include separate lumens and openings that are then joined or integrated into a single lumen. Such a configuration may stabilize the medical instruments separately while ultimately guiding the medical instruments substantially along the same path.

Figure 9:
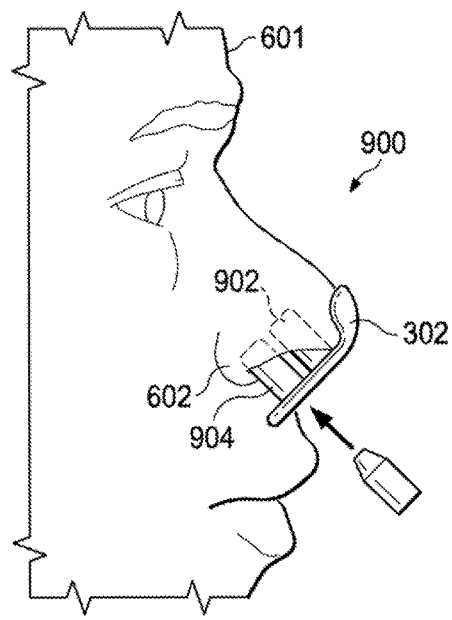
FIG. 9 is a schematic, side-view of another nasal guide in accordance with an illustrative embodiment.

FIG. 9 is a schematic, side-view of a nasal guide 900 in accordance with an illustrative embodiment. The nasal guide 900 may include multiple openings with walls or supports defining the lumens 902 and 904 that extend inward to a nasal cavity of a patient. In one embodiment, the lumens 902 and 904 may be defined separately and extend from the supports 302 (and 304 not shown) of the nasal guide 900. The lumens 902 and 904 may have a gap, or notch, between them.

Figure 10:
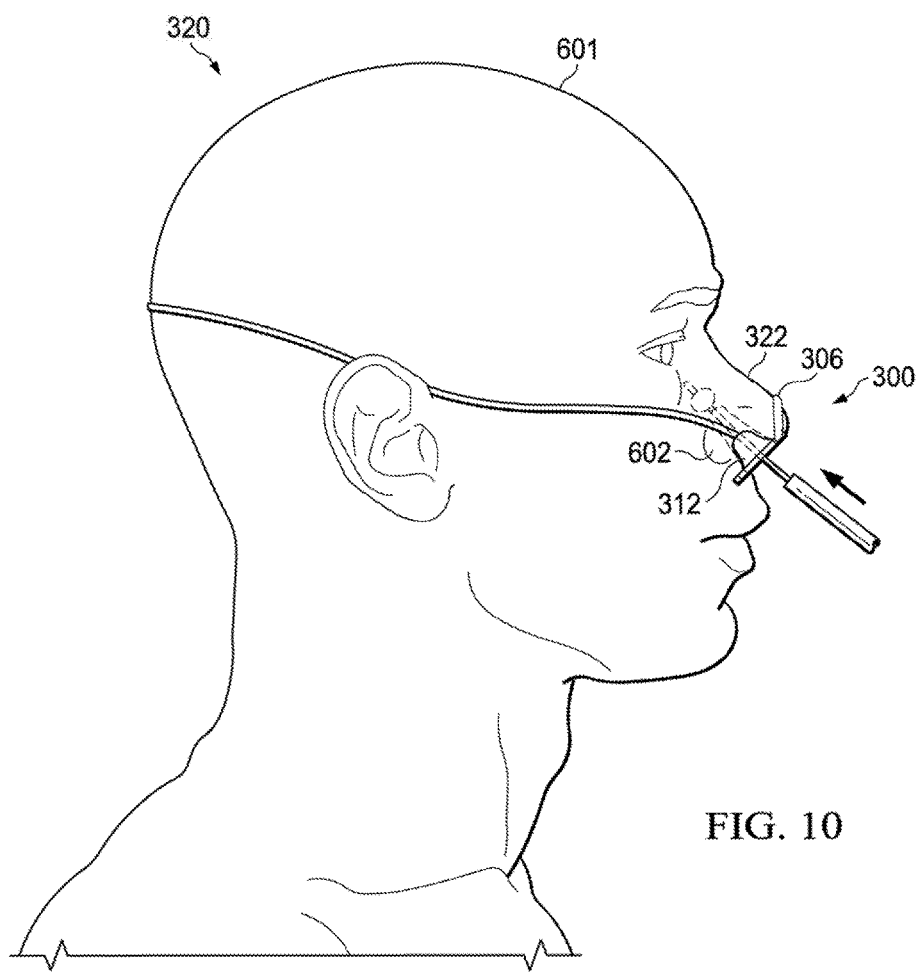
FIG. 10 is a schematic, side view of a nasal guide being utilized on a patient in accordance with an illustrative embodiment.

FIG. 10 is a schematic, side-view of the nasal guide 300 being utilized on a patient 601 in accordance with an illustrative embodiment. In one embodiment, the nasal guide 300 may be utilized to protect the nose 602 of the patient 601 during a medical procedure, such as balloon sinuplasty. The bridge 306 may touch the nose 602 of the patient 601 during use. The lateral edges 312 may abut the lateral edges of the nostrils to provide lateral support.

Figure 11:
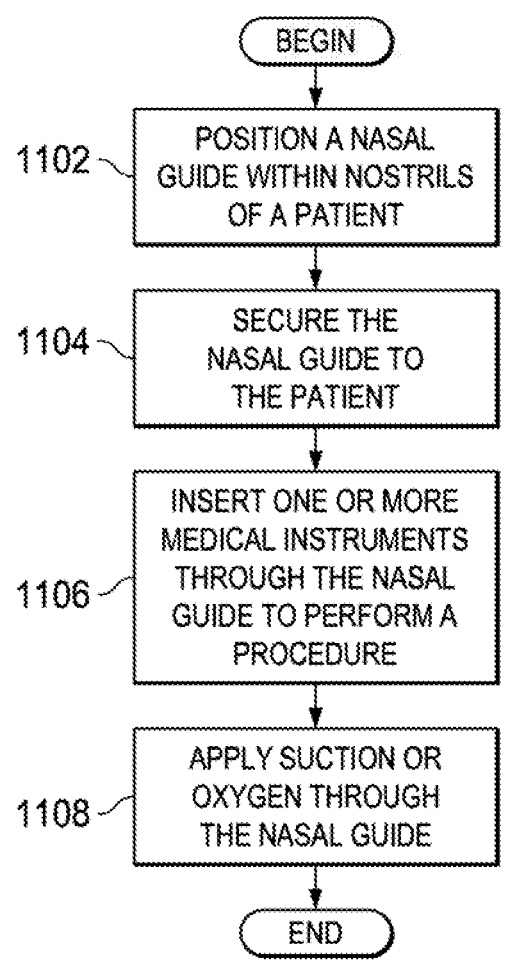
FIG. 11 is a flowchart of a process for utilizing a nasal guide in accordance with an illustrative embodiment.

FIG. 11 is a flowchart of a process for utilizing a nasal guide in accordance with an illustrative embodiment. The process of FIG. 11 may be implemented by a medical professional, or any other person, utilizing a nasal guide on a patient as is illustrated in FIGS. 6 and 10.

The process may begin with the medical professional positioning a nasal guide within nostrils of a patient (step 1102). In one embodiment, only the lumens (and supporting framework) of the nasal guide are inserted into the nostrils extending to the nasal cavity of the patient. The medical professional may select the nasal guide based on the size and shape of the nose of the patient. For example, the selected nasal guide may be substantially smaller for a child. The nasal guide may also be selected based on the size and shape of the medical instruments that are utilized in performing the procedure. For example, a light source and an endoscope with a balloon may need to be inserted into the nostrils simultaneously. As a result, the medical professional may select a nasal guide with two lumens. In another embodiment, the guide is configured to receive a wired or portable endoscope or other medical instrument through naturally or surgically-created openings, including, but not limited to, laparoscopic, abdominal, pelvic, chest, head, neck, intracranial, ear, extremity, cardiac or vascular procedures or diagnostic evaluations.

In another embodiment, the nasal guide may be created, customized, molded, or manufactured to meet the size and shape of a particular patient's nose. In addition, the medical professional may select nasal guide attachments that may be attached to the nasal guide to apply suction and/or oxygen to the patient before, during, or after the medical procedure. The nasal guide may also be configured to act as a wave guide, be illuminated, or glow in the dark. For example, a light source, when shined into the nasal guide, may light up the interior and exterior portions of the nasal guide.

In one embodiment, the portion of the nasal guide that is inserted within the nostril(s) may have a conical shape for enlarging the nostrils as the nasal guide is drawn into the nostril(s) of the patient by a securing mechanism, such as an elastic fastened around the neck or head of the patient. The elastic or securing band may gently open the nostrils to provide easier access to the nasal cavities and sinuses.

Next, the medical professional secures the nasal guide to the patient (step 1104). As previously described, the nasal guide may be secured in any number of ways, including elastics, headgear, straps, clips, adhesives, draped configurations, and so forth. The nasal guide may be adjustable (e.g., tightening bands, Velcro, securing holes, etc.) and may be secured to any portion of the body, clothes, or accessories of the patient, such as any portion of the head, neck, or ears.

The nasal guide may also be connected to protective glasses. In one embodiment, the securing portion of the nasal guide is draped around the ears of a patient similar to a nasal cannula.

Next, the medical professional inserts one or more medical instruments through the nasal guide to perform a procedure (step 1106). The medical instruments may be inserted into and retracted from the nostrils and nasal passage any number of times. The nasal guide guides the medical instruments into the nasal passage during insertion. In one example detailing use of the nasal guide, a single medical professional rather than multiple medical professionals may perform a medical procedure. The nasal guide may be utilized to ensure that the medical instruments are positioned correctly to prevent abrasion, stabbing, or scraping the bone or tissue within the nasal passages or the interior and exterior of the nostrils. In addition, the nasal guide may stabilize the instruments in the nose to allow for ease of manipulation during the procedures especially if the patient moves or sneezes.

In one embodiment, the medical professional may apply suction or oxygen through the nasal guide (step 1108). The nasal guide may be utilized to provide suction or oxygen before, during, or after the procedure. For example, the nasal guide may be configured for simultaneously performing the medical procedure through a first lumen as well as applying suction or oxygen through a second lumen or through a separate side of the nasal guide. An attachment or insert may be built-in, inserted, or attached to the nasal guide to apply suction or oxygen for the patient. In one example, one or more adapters may be inserted or screwed into the openings of the lumens to provide suction or oxygen to the patient. Application of suction or oxygen through the nasal guide provides flexibility for rapidly-developing situations. For example, immediately after a surgery a patient may need to receive oxygen to stimulate recovery. As a result, the nasal guide may serve a dual-purpose. In addition, the nasal guide may be utilized to secure oxygen or apply suction for patients that are seizing, moving, or otherwise unable to receive oxygen or suction through traditional means.

Figure 12:
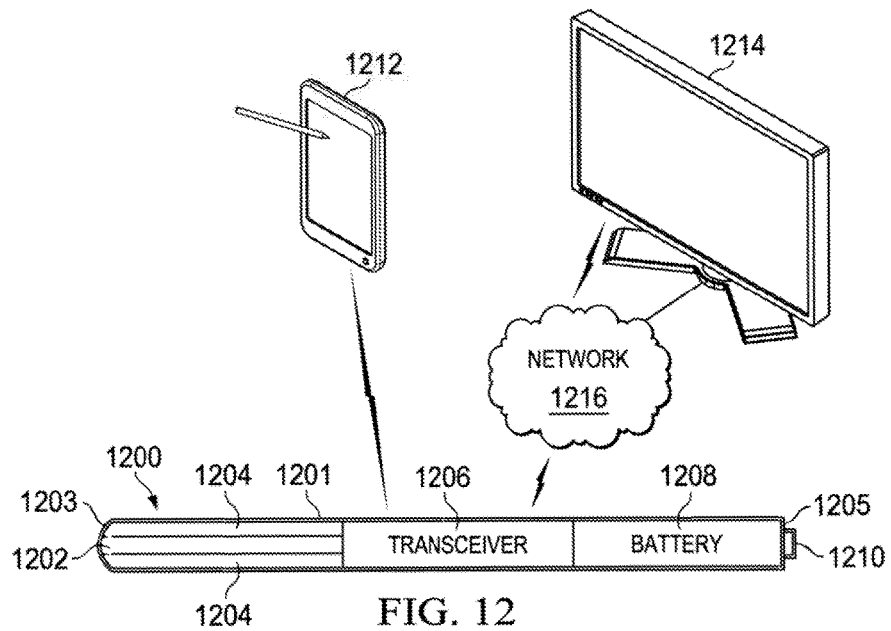
FIG. 12 is a schematic, pictorial representation of a portable endoscope in accordance with an illustrative embodiment.
Figure 13:
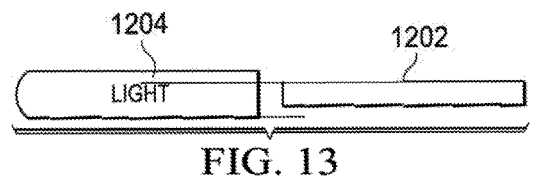
FIG. 13 is a schematic, side view of a cylindrical light and camera in accordance with an illustrative embodiment.
Figure 15:
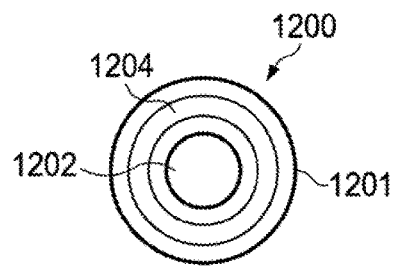

Turning now to FIGS. 12, 13 and 15, a schematic, pictorial representation of a portable endoscope 1200 is shown in accordance with illustrative embodiments. An endoscope is an instrument that may be introduced into the body of an individual or patient to give a view of internal parts. The portable endoscope 1200 may be utilized in very small spaces and may be easier to use than existing endoscopes. Existing endoscopes are generally bulky and not ergonomically shaped and may require two or more medical professionals to operate effectively (e.g. a doctor and nurse). In one embodiment, the portable endoscope 1200 is a wireless scope that is condensed into a reduced footprint or size. The portable endoscope 1200 may be utilized by a single user or positioned a single time or as needed within a nasal guide to free up hands of the medical professional.

The portable endoscope 1200 may be cleaned for repeated use or may be a disposable one-time use portable endoscope 1200. The portable endoscope 1200 may be a wand or cylindrical-shape for easy handling by a medical professional. In one embodiment, the portable endoscope has a diameter or cross-sectional measurement of between 1 mm to 5 mm, although the diameter may vary widely depending on the particular application.

The portable endoscope 1200 may be a stand-alone device or may be utilized or integrated with the nasal guide as herein described. For example, the portable endoscope 1200 may be built into one or more of the lumens of the nasal guide. The portable endoscope 1200 may also be attached to or inserted into the nasal guide.

Figure 14:
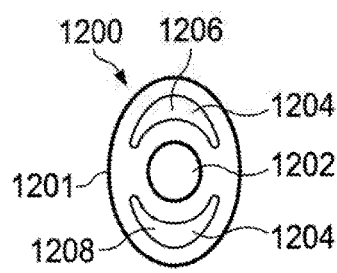
FIGS. 14 and 15 are schematic, front views of portable endoscopes in accordance with illustrative embodiments.

As exemplified in the schematic front views of FIGS. 14 and 15, the portable endoscope 1200 may be shaped as a circle, rounded square, oval, ellipse, rounded triangle, or any other shape. The portable endoscope 1200 may be utilized for any number of medical or non-medical procedures or examinations that are known in the art. In one embodiment, the portable endoscope 1200 is configured to be received by an opening, lumen, or port of the nasal guide as herein described. The portable endoscope 1200 may be inserted to a required depth and positioned to display a video image to the medical professional. In one embodiment, friction, tight tolerances, or interference fittings of the opening and external dimensions of the portable endoscope 1200 may be utilized to secure the portable endoscope 1200 in the nasal guide. In an alternative embodiment, the nasal guide may include a positioning motor for moving the portable endoscope 1200 in and out, rotating the portable endoscope 1200, or otherwise positioning the portable endoscope 1200 within the examined space. The same positioning feature may be performed for a camera 1202 without moving the portable endoscope.

In one embodiment, the portable endoscope 1200 may include the camera 1202, a light 1204, a transceiver 1206, a battery 1208, and a switch 1210. The portable endoscope 1200 may be enclosed in a case 1201. In one embodiment, the case 1201 is a waterproof framework completely sealing in and securing the components of the portable endoscope. The case 1201 may include any number of seals and watertight connections ensuring that the portable endoscope 1200 may be utilized multiple times without damage from fluids. For example, the case 1201 may be formed entirely of a metal, polymer, plastic, or glass. In another embodiment, different components and materials may be fused together. For example, the main body of the case 1201 may be formed of stainless steel with a glass end or lens for the light 1204 to shine through and the camera 1202 to retrieve video images.

In one embodiment, the case 1201 includes the contacts, interfaces, wires, or busses for each of the internal electrical components. For example, the camera 1202 and/or light 1204 may contact a video bus integrated within the frame or case 1201 for transmitting the video signal to the transceiver 1206 for transmission. The light 1204 may also include an interface for communicating video signals from the camera 1202 to the case 1201 or directly to the transceiver 1206. In one embodiment, the bus for sending and receiving video or commands may be insulated or the case 1201 may include a designated space ensuring that none of the components contact the bus. Likewise, a wire or power conduit integrated within the case 1201 may communicate an electrical energy signal from the battery 1208 to the transceiver 1206, light 1204, and/or camera 1202. Alternatively, the electrical components may be serially connected in the positioned order for both powering the components and communicating a video signal (and command signals as needed).

A first end 1203 of the case 1201 may include or be formed of a lens or transparent plastic cover focusing or allowing light to be acquired as video content by the camera 1202. Any number of lenses may be utilized depending on the medical procedure being performed. For example, the lens may be a simple convex, biconvex, plano-convex, positive meniscus, negative meniscus, plano-concave, macro, zoom, apochromat, process, fisheye, stereoscopic, infrared, ultraviolet, swivel, biconcave, etc. lens. The lens may also be selected to prevent fluids from accumulating on the camera 1202 and light 1204 blocking the view of the relevant site.

In one embodiment, the camera 1202 is a condensed digital video camera configured for wirelessly communicating the video content through the transceiver 1206. The camera 1202 may be configured to capture video in response to the output of the light 1204 which may broadcast visible light, specific spectrums, infrared, ultrasound, ultra violet, x-ray, gamma ray, or other electromagnetic or non-electromagnetic imaging. In one embodiment, the light 1204 may be a fiber optic light that is powered by external sources. Any kind of digital or fiberoptic imaging or viewing device may be used may be used for the camera 1202 and the light 1204. In one embodiment, the camera is a charge coupled device (CCD) camera, such as a CMOS camera composed of multiple stacked and interconnected semiconductor layers. The camera 1202 may be configured or selected to correspond to, pick-up, or capture the type of light 1204 inserted or installed in the portable endoscope 1200. The camera 1202 may be manually or remotely controllable. For example, the camera 1202 may include a swivel lens that rotates to give unique perspectives and camera angles. The lens or camera 1202 may be configured to protrude from or extends from the portable endoscope 1200. In another embodiment, the camera 1202 may be a fiber optic camera.

The camera 1202 may utilize any number of electronic or even vibrational spectra for chemical analysis, oximetry, disease classification, and molecular microscopy. For example, the camera 1202 may also be configured to include features of a microscope. In addition, diffuse reflection, fluorescence reflectance (fluorescence spectroscopy), Raman reflectance (Raman spectroscopy), and absorption may be observed, measured, or recorded by the camera 1202. The wavelength or spectrum produced by the light 1204 may affect the light 1204 and camera 1202 selected for the portable endoscope 1200. The camera 1202 may be configured to produce 1-D spatial information utilizing a single wavelength or spectrum, 2-D spatial information utilizing wide-field spectroscopy/hyperspectral imaging, and 3-D spatial information utilizing tomography. The camera 1202 may be selected for a particular light 1204 or based on characteristics of the camera 1202 or generated video signal including resolution, intensity, frame rate, signal-to-noise ratio (SNR), peak SNR, noise immunity, timing, scanning, and so forth.

The video captured by the video camera may be transmitted directly or indirectly to the wireless device 1212 or computing device 1214. For example, the portable endoscope 1200 may wirelessly communicate with the computing device through a network 1216. The network 1216 may utilize a communication standard, such as 802.11_ (e.g 802.11n) as the standard continues to be updated. The direct or indirect communications may represent Bluetooth, Zig-Bee, WiFi, ultra-wideband, wireless USB, infrared, wireless local area network (WLAN), WiMAX, proprietary standards, or other radio frequency signals whether analog or digital that may be utilized to communicate a video signal. Any number of FCC, FDA, IEEE, ISO, CEN, ETSI, ARIB, ANSI, or IEC approved communications protocols or standards may also be transmitted by the transceiver 1206. The transceiver 1206 as well as the transceiver (not shown) of the wireless device 1212 or computing device 1214 may include any of the components necessary for communicating utilizing these standards. Indeed, the types of wireless or wired standards or methods of communication are numerous.

In one embodiment, an antenna (not shown) may be built into the transceiver 1206. The antenna may also be a wire antenna that extends from a second end 1205 of the case 1201 to establish a stronger wireless signal. In another embodiment, the case 1201 may be connected to the transceiver 1206 allowing all or portions of the case 1201 to act as the antenna for the transceiver 1206.

The video signal may be received and displayed by the wireless device 1212 and/or computing device 1214 in real-time. The video signal may be formatted before or after being sent from the portable endoscope 1200. In one embodiment, the portable endoscope 1200 may include a processor, ASIC, FPGA, and/or other logic for managing the portable endoscope 1200 and processing the video signals. The video may be compressed in a raw or formatted state for communication by the transceiver 1206. For example, the video content may be packetized and communicated with or without error detection and known packet analysis, processing, decryption, and other similar steps may be performed by a receiving device. In one embodiment, the portable endoscope 1200 may include a memory for storing the video content for subsequent analysis, review, documentation, training, or educational purposes. Alternatively, the video may be recorded by the wireless device 1212 or computing device 1214 for the same reasons. The wireless device 1212 and computing device 1214 may also act as a server to deliver or save content to any number of other client devices, systems, equipment, streaming configurations, or databases.

In another embodiment, a cable or wire may be utilized to communicate the video directly to the wireless device 1212, computing device 1214, or to an external transceiver that is not integrated with the case 1201 of the portable endoscope. (see, e.g., FIG. 16 below). The same cable may also be utilized to power the portable endoscope 1200 from a remote location further reducing the required size of the portable endoscope 1200. For example, a USB cable (standard, mini, micro, etc.) connected to the portable endoscope 1200 and wireless device 1212 may both power the portable endoscope 1200 and communicate video to the wireless device 1212.

A second end 1205 of the case 1201 may be removable for inserting or removing the components of the portable endoscope 1200. For example, the second end 1205 of the case 1201 may snap in, interconnect, latch, or include threads for securing the components of the case 1201. The portable endoscope 1200 may communicate with the wireless device 1212 or the computing device 1214.

In one embodiment, the components of the portable endoscope 1200 may be interchangeable. For example, even the relative positioning of components, such as the transceiver 1206 and battery 1208 may be varied. For example, the transceiver 1206 may more efficiently transmit and receive signals when positioned at the second end 1205 of the portable endoscope 1200 where the battery 1208 is shown. As a result, the portable endoscope 1200 may be configured for each patient or medical professional. For example, different cameras or batteries may be inserted into the case 1201 for different situations. In one embodiment, the camera 1202, which may include a video camera, may be an infrared camera or spectrum-specific camera configured to view blood flow (or the lack thereof) within the nose. In another embodiment, the components of the portable endoscope 1200 are permanently connected.

In one embodiment, the components of the portable endoscope 1200 are powered by the battery 1208. The battery 1208 may be a high-powered energy storage device. For example, the battery 1208 may be a rechargeable or one-time use polymer battery, alkaline, zinc-air battery, lithium ion battery, thin film battery, ultracapacitor, fuel cell, piezo electric generator, or other capacitors or batteries being developed and known in the art. The portable endoscope 1200 may be utilized repeatedly by replacing the battery 1208 as needed.

In another embodiment, the portable endoscope 1200 may include a port (not shown) for recharging the battery 1208 without removing the battery 1208 from the case 1201. Similarly, the portable endoscope 1200 may be configured to function in a wireless or wired state. For example, the portable endoscope 1200 may be connected directly to the computing device 1214 utilizing a cable, bus, wire, or connector, such as a micro-USB to USB connector for communicating video content. Additionally, the portable endoscope 1200 may not include the battery 1208 and instead may be powered and display video content through the wireless device 1212 or computing device 1214. For example, if the medical professional utilizes the wireless features of the portable endoscope draining the battery 1208, the portable endoscope 1200 may be connected to the computing device 1214 for the additional power requirements while simultaneously charging the battery 1208 for subsequent wireless usage. In another embodiment, the portable endoscope 1200 may be capable of being directly charged by, e.g., a wall outlet or other stationary or semi-stationary form of power supply.

In one embodiment, the camera 1202, light 1204, transceiver 1206, and battery 1208 may be interconnected by magnetic contacts, leads, pins, or connectors (not shown). The magnetic contacts automatically align and attach the components when placed in proximity to one another. As a result, a medical professional or other individual may easily add or remove the various electrical components of the portable endoscope and know that the components will self-attach when placed in proximity to one another. The magnetic leads may include contacts for power, logic, or command signals, as well as video communications between each component.

In another embodiment, leads, wires, traces, contacts, or connectors may be integrated with or built into the case 1201 for communicating power, video, control signals, or other signals between the camera 1202, transceiver 1206, and battery 1208 which may also include contacts or leads for interfacing with the case 1201. The case 1201 may also include insulators that prevent bleed over, noise, and crosstalk to keep the distinct signals separate for each portion of the trace. In another embodiment, the camera 1202, transceiver 1206, and battery 1208, and other described components may communicate signals utilizing ports, contacts, adapters, or male and female connectors. For example, the connectors may be pin, sleeve, and socket connectors of a reduced size, such as a version of a mini-DIN, S-video, DVI, USB, coaxial, or HDMI connectors (micro video connectors). However, any other form of standard or proprietary connectors may be utilized to connect the electrical components. For example, the connectors may have a footprint of 0.25 mm-1 cm (diameter, area, length, etc), however, larger and smaller footprints are also possible. In addition, the diameter of the portable endoscope 1200 may vary between 0.1 mm and 1.5 cm with other sizes being produced for different applications. For example, the portable endoscope 1200 may vary in size from pencil or straw sized to coffee straw or needle sized based on the type of manufacturing and design processes utilized for the portable endoscope 1200.

The components of the portable endoscope 1200 may include longitudinal or lateral ridges, notches, or other alignment structures for properly aligning a component, such as the light 1204 and camera 1202 within the transceiver 1206 and battery 1208. For example, a ridge (not shown) along the top of the cylindrically-shaped camera 1202 may prevent the camera 1202 from being inserted in the light 1204 except when in the proper alignment. Similar ridges may be included on the light 1204, transceiver 1206, battery 1208, and logic if present. A corresponding notch on the case 1201 may align the components.

In another embodiment, portions or components of the portable endoscope 1200 may be separated by flexible connectors (not shown) (e.g., centipede configuration) that allow distinct components or portions of the portable endoscope 1200 to be individually angled and positioned. For example, wired connectors between each component of the portable endoscope 1200, such as a bus configured to communicate video signals and power, may enhance flexibility. For example, the light 1204 and camera 1202 portion of the portable endoscope 1200 may be angled a particular direction, relative to the remainder of the portable endoscope 1200, before insertion into the nose to view a selected sinus. The separated flexible portions of the portable endoscope 1200 may be manually adjusted or controlled by one or more servos. In one example, a mechanical pivot that provides resistive adjustments may be twisted to achieve the desired configuration of the portable endoscope. For example, a graphical user interface accessible through the computing device 1214 may be utilized to receive user selections or commands to pivot or rotate the portion of the portable endoscope 1200 including the camera 1202 and light 1204.

The electrical components of the portable endoscope 1200 may be manufactured utilizing processes for plastic, organic, and inorganic semiconductors, substrates, electronics, and logic. For example, the light 1204, transceiver 1206, and battery 1208 may include flexible plastic-based substrates that function with printable conductive inks, organic light-emitting diode (OLED) layers and materials, and/or active-matrix thin-film-transistor arrays. Multilayer composite structures may be utilized to create and manufacture the portable endoscope. For example, roll-to-roll processing with inkjet printing or spray deposition may be utilized to produce the flexible and reduced footprint components of the portable endoscope 1200. In one embodiment, the entire portable endoscope 1200 may be configured to flex to be moved and positioned to the correct location. Magnetic coupling, wires, and MEMs connections may be utilized to bend and flex the portable endoscope 1200.

FIG. 13 is a schematic, side-view of a light 1204 and camera 1202 in accordance with an illustrative embodiment. In one embodiment, the camera 1202 is cylindrically shaped and is inserted or partially encased in the light 1204. The light 1204 may be doughnut, or annular, shaped and configured to receive the camera 1202. During assembly of the various parts, the light 1204 and camera 1202 may be changed out as has previously been described.

In another embodiment, the camera and light 1204 may both be stacked or placed side by side. Alternatively, the camera 1202 and/or light 1204 may utilize different shapes, such as an ellipse, semi-circle, square, rectangle, or oval.

FIGS. 14 and 15 are schematic front views of the portable endoscope 1200 in accordance with illustrative embodiments. FIG. 14 illustrates the portable endoscope 1220 shaped as an oval. The light 1204 may be formed from boomerang-shaped lights. The light 1204 may emit a single spectrum of light or distinct spectra depending on the needs of the medical professional. For example, an upper portion 1206 of the light may be a miniaturized halogen light configured to emit a bright white light and the lower portion 1208 of the light may be an infrared LED that may be activated as needed. In one embodiment, the light 1204 and camera 1202 may directly abut each other. In another embodiment, any number of spacers or separators may be built into the case 1201, camera 1202, or light 1204 to correctly position the various components.

FIG. 15 illustrates the portable endoscope 1200 of FIG. 13 with a camera 1202 and a surrounding light 1204. The light 1204 may be a single light or may be composed of multiple lights that transmit light or signals at different frequencies or intensities. For example, different lights may be turned on at different times to examine cartilage, bone, blood flow, skin, or other forms of tissue. In one embodiment, the camera 1202 may fixedly or movably extend or protrude from the end of the portable endoscope 1200 to provide an uninhibited view of portions of the body during use.

In one embodiment, the camera 1202 may be connected to a motor that allows the camera 1202 to extend a small distance from the end of the portable endoscope 1204, rotate, and/or pivot. For example, the case 1201 may include bearings or rollers (not shown) for extending and rotating the camera 1202. The motor may be controlled remotely utilizing logic included in the portable endoscope 1200. For example, the wireless device 1212 of FIG. 12 may include a graphical user interface for rotating or pivoting the camera 1202, extending the camera 1202, switching between light spectrums, and recording video content. The portable endoscope 1200 including the switch 1210 (shown in FIG. 12) may also include controls for these functions as well. In addition, the camera 1202 may be able to zoom in and out. In one embodiment, the camera 1202 may utilize a fly eye configuration to get multiple views.

Figure 16:
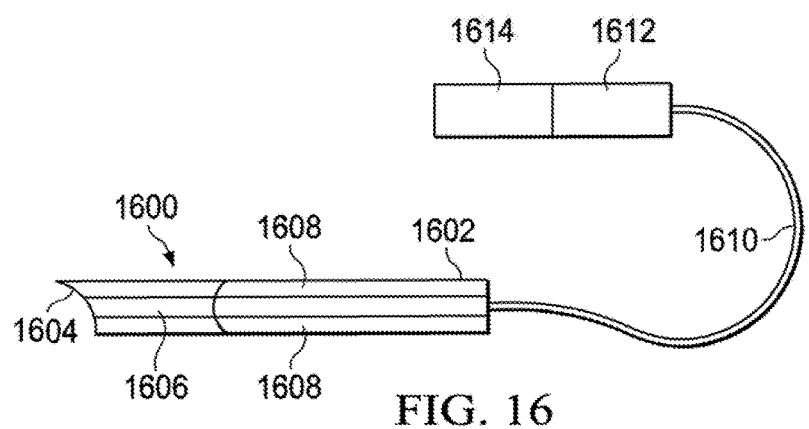
FIG. 16 is a schematic, pictorial representation of the portable endoscope in accordance with an illustrative embodiment.

FIG. 16 illustrates another embodiment of a portable endoscope 1600. The portable endoscope 1600 may include a case 1602, first end 1604, camera 1606, light 1608, cable 1610, transceiver 1612, and battery 1614. The portable endoscope 1600 is externally connected to the transceiver 1612 and battery 1614. As a result, the size of the portable endoscope 1600 may be reduced even further.

In one embodiment, the cable 1610 of the portable endoscope 1600 is incorporated into an elastic, Velcro band, or securing component for the nasal guide. The cable 1610 may include a video cable for communicating a video signal to the transceiver 1612 as well as a wire for providing power. The transceiver 1612 and battery 1614 may be attached or integrated into the securing component of the nasal guide. For example, the Velcro band may include a pocket for inserting the transceiver 1612 and battery 1614, and the cable 1610 may be built in. In one embodiment, the transceiver 1612 may also include a port (not shown) for connecting the portable endoscope 1600 to a wireless device or computing device to view the video content and perform the medical procedure with the visual assistance of the portable endoscope 1600.

The first end 1604 of the portable endoscope 1600 may have a diagonal concave shape for preventing blood, mucous, pus, or other fluids from accumulating on the first end 1604 thereby blocking the view of the camera 1606 and the output of the light 1608. Blood that accumulates on the first end 1604 preferably runs to the bottom or side of the portable endoscope 1600 because of the shape.

In another embodiment, the first end 1604 may be rounded with an even concave shape that pushes or maintains an air bubble in front of the first end 1604 of the portable endoscope 1600 during utilization keeping the camera 1606 unobstructed.

Figure 17:
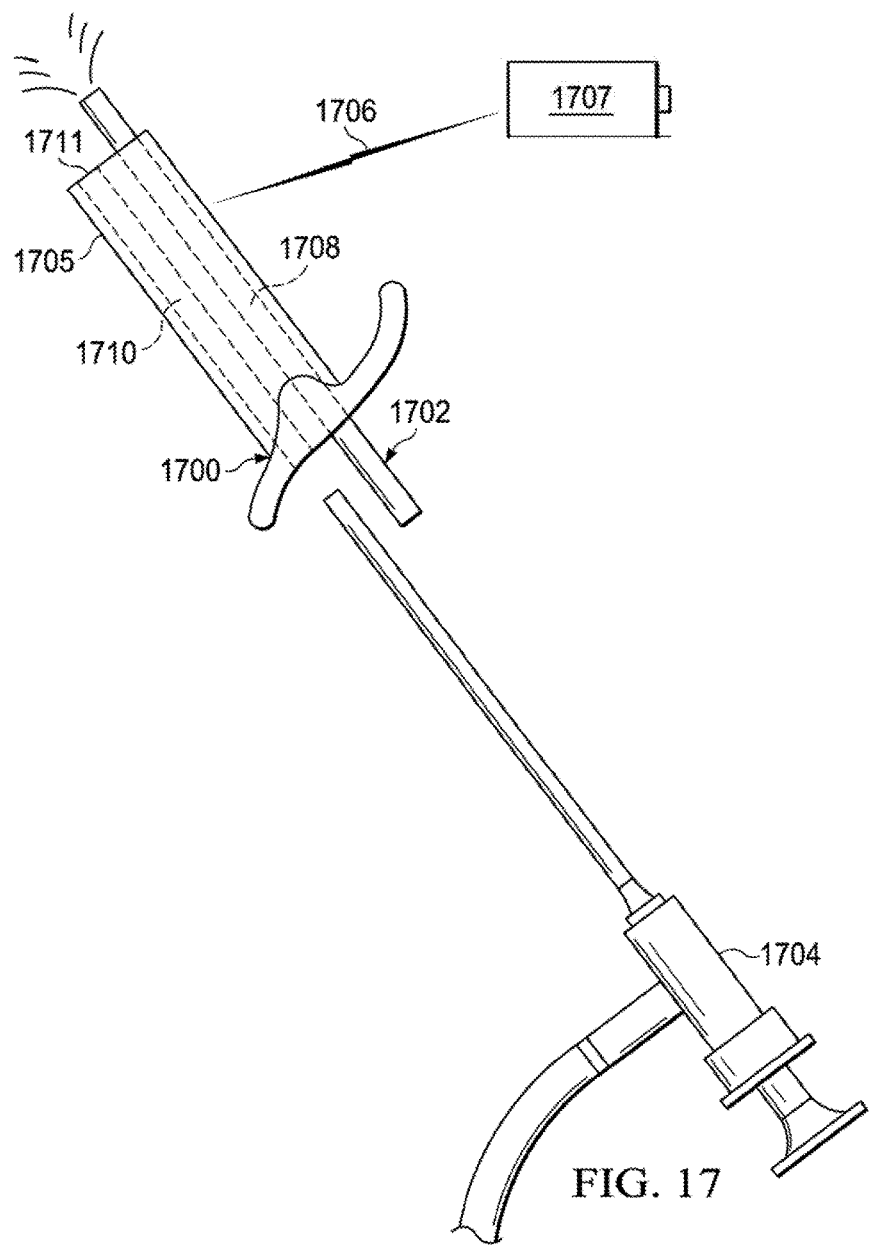
FIG. 17 is a schematic, pictorial representation of a nasal guide being utilized with a portable endoscope and a balloon catheter in accordance with an illustrative embodiment.

FIG. 17 is a schematic, pictorial representation of a nasal guide 1700 being utilized with a portable endoscope 1702 and a balloon catheter 1704 in accordance with an illustrative embodiment. The balloon catheter 1704 may be a medical device, endoscope, catheter, technology, or system, such as those sold by Acclarent™. In one embodiment, the medical professional may insert and position the nasal guide 1700 in the nose of the patient as previously described. In this embodiment, the nasal guide 1700 includes an elongated frame 1705 enclosing a first lumen 1708 and a second lumen 1710. The lumens 1708, 1710 of the nasal guide 1700 are elongated to reach further into the nasal cavity of the patient toward the sinuses for performing various medical procedures. As previously described, the elongated frame 1705 may be funnel or coned shaped or narrow slightly at one end to facilitate expansion of the nostrils and to reach further into the nasal cavities as the nasal cavities narrow.

The portable endoscope 1702 and balloon catheter 1704 may be positioned in either the first lumen 1708 or the second lumen 1710 of the nasal guide. In one embodiment, the nasal guide 1700 may include the first lumen 1708 and second lumen 1710 for both nostrils and the portable endoscope 1702 and balloon catheter 1704 may be moved between any of those lumens based on the physical condition of the patient, medical procedure being performed, and/or preferences of the medical professional.

Next, the portable endoscope 1702 may be inserted through the first lumen 1708 of the nasal guide 1700 to the nasal cavity of the patient. The portable endoscope 1702 may be turned on and activated to begin communicating video through a wireless signal 1706 to a wireless adapter 1707, wireless device, or computing device as previously described. The wireless adapter 1707 may be utilized with any number of electronic devices to receive or format the video content in real-time. In one embodiment, the wireless adapter 1707 is an adapter, such as a USB adapter, dongle, or other wireless interface configured to receive wireless communications from the portable endoscope 1702, and may decode, decrypt, and/or format the video signal retrieved by the camera of the portable endoscope 1702 for view by a medical professional or other party. The wireless adapter 1707 may utilize any of the standards are previously described to communicate with the portable endoscope 1702.

The portable endoscope 1702 may be secured by the nasal guide 1700 at a desired position and location selected by the medical professional. The portable endoscope 1702 may easily be further inserted, removed, or rotated. The video provided by the portable endoscope 1702 may be communicated to one or more other devices for guiding or informing the medical professional while performing a medical procedure. The portable endoscope 1702 may provide both light and video within the nasal or body cavity or other orifice. The light and video may be utilized to position and utilize the balloon catheter 1704. For example, the video from the portable endoscope 1702 may ensure that a wire and balloon inserted through the balloon catheter are guided into a selected sinus for performing a procedure, such as balloon sinuplasty.

In another embodiment, the portable endoscope 1702 may include a motorized end for controlling the positioning of the inserted end with the light and camera. For example, the portable endoscope 1702 may pivot 90° and rotate 360°. In addition, the light and camera may be configured to be extended or retracted from the frame of the portable endoscope 1702. For example, a graphical user interface of an iPad, tablet, or other computing device may be utilized to vertically and horizontally position and angle the portable endoscope (and corresponding light and camera) to a desired position to illuminate tissue and provide video guidance of the balloon catheter 1704 and insertion of a wired balloon into one or more sinuses.

In another embodiment, the first lumen 1708 or the second lumen 1710 may be enclosed or sealed on an interior end 1711. As a result, a non-medical scope, borescope, probe, or other instrument may be inserted into the nasal guide 1700 without requiring an FDA-approved device or extensive sanitation. The sealed end of the lumen may be formed of a transparent glass or plastic for videoing through the nasal guide 1700. In another embodiment, the nasal guide 1700 includes extensions (not shown) sized only slightly bigger than the first lumen 1708 or second lumen 1710 for extending the reach of the openings. The extensions may be straw-like extensions that further extend the reach of the nasal guide 1700 and may be open ended or enclosed. Depending on the configuration of the nasal guide 1700 as have been illustrated in the previous embodiments, the extensions may extend from 1 cm to 20 cm from the end of the elongated frame 1705, but the distance may vary from this depending on the procedure or application.

In another embodiment, the extensions or the elongated frame 1705 of the nasal guide 1700 may include corrugations (not shown) like a flexible straw for angling or positioning the first lumen 1708 and second lumen 1710. For example, the nasal guide 1700 may be manually bent or configured particularly at the corrugations to enhance performance of the medical procedure and the nose of the patient. Similarly, a portion of the frame 1705 of the portable endoscope 1702 may be corrugated for manually, mechanically, or electrically configuring the shape and direction of the portable endoscope 1702.

The previous detailed description is of a small number of embodiments for implementing the invention and is not intended to be limiting in scope. In particular, components and features of the different embodiments, such as embodiments of the nasal guide and portable endoscope, may be combined in any number of possible combinations that are not described herein for purposes of brevity. The following claims set forth a number of the embodiments of the invention disclosed with greater particularity.

What is claimed:

1. A method for performing internal imaging, comprising:
providing a wireless endoscope, the wireless endoscope being portable, the wireless endoscope including a first portion and a second portion, the first portion and the second portion are cylindrical bodies without protrusions or ports on their outer circumferential surfaces, the first portion of the wireless endoscope including at least a lens, camera, and light, the first portion connected to the second portion of the wireless endoscope, the camera and the light are interchangeable in ordinary use, the second portion including at least a battery and a transceiver, and the first portion is configured to be inserted into a body while the second portion is configured to remain outside the body;
powering on the wireless endoscope in response to receiving user input from a user;
emitting light from a distal end of the first portion proximate the lens utilizing the light;
adjusting light emitted from the light of the wireless endoscope utilizing a user interface;
capturing video inside the body utilizing the camera in communication with the lens;
controlling the light and the camera utilizing the user interface;
and
wirelessly communicating the video from the transceiver to an external receiver associated with a display.

2. The method of claim 1, further comprising:
connecting the first portion with the second portion utilizing a connector, wherein the first portion of the wireless endoscope is configured for insertion into the body and
visualizing the nasal cavities.

3. The method of claim 2, wherein the user interface is presented to a user by a wireless device in communication with the wireless endoscope.

4. The method of claim 1, wherein the video is communicated in real-time, and wherein neither the first portion nor the second portion of the wireless endoscope are ingested.

5. The method of claim 1, further comprising:
recording the video to a memory in response to user input.

6. The method of claim 1, wherein one or more of the transceiver and battery are interchangeable.

7. The method of claim 1, further comprising:
formatting the video for communication to the external receiver in response to capturing the video.

8. The method of claim 7, wherein the communicating is performed directly between the wireless endoscope and the external receiver.

9. The method of claim 1, wherein the lens covers the camera and the light.

10. The method of claim 1, wherein the user interface is integrated with one or more surfaces of the second portion of the wireless endoscope.

11. The method of claim 1, further comprising:
performing error detection and processing off the video.

12. A method for performing internal imaging, comprising:
providing a wireless endoscope, the wireless endoscope being portable, the wireless endoscope including a first portion and a second portion, the first portion and the second portion are cylindrical bodies without protrusions or ports on their outer circumferential surfaces, the first portion of the wireless endoscope including at least a lens, camera, and light, the first portion connected to the second portion of the wireless endoscope, the camera and the light are interchangeable in ordinary use, the second portion including at least a transceiver and a rechargeable battery;
powering on the light and a camera in response to user input;
emitting light from a distal end of the first portion proximate the lens utilizing the light;
adjusting light emitted from wireless endoscope;
capturing video utilizing the camera in communication with the lens, wherein the first portion of the wireless endoscope is inserted into a body while the second portion of the wireless endoscope remains outside the body;
controlling at least the light and the camera utilizing a user interface controlled by a user;
and
wirelessly communicating the video from the transceiver to a receiver associated with a display utilized to display the video.

13. The method of claim 12, wherein the first portion is connected to the second portion utilizing a connector, and wherein the diameter of the first portion is adapted for viewing sinuses.

14. The method of claim 12, wherein the light, the camera, the transceiver and the battery are interchangeable.

15. The method of claim 12, wherein the user interface is presented to the user through a wireless device in communication with the wireless endoscope.

16. The method of claim 12, further comprising:
formatting the video for wireless communication to the receiver associated with the display device in response to capturing the video.

17. The method of claim 12, further comprising:
recording the video in response to a user selection.

18. The method of claim 12, wherein the user interface is integrated with an outer surface of the second portion.

19. A method for performing internal imaging, comprising:
providing a wireless endoscope, the wireless endoscope being portable, the wireless endoscope including a first portion and a second portion, the first portion and the second portion are cylindrical bodies without protrusions or ports on their outer circumferential surfaces, the first portion of the wireless endoscope including a lens, camera, and light, the first portion connected to the second portion of the wireless endoscope, the camera and the light are interchangeable in ordinary use, and the first portion is configured for insertion into the body and to visualize internal portions of a body;
receiving a rechargeable battery for electrical connection in the second portion;
powering on the light and a camera in response to user input;
emitting light from a distal portion of the light proximate the lens, wherein neither the first portion nor the second portion are ingested in the body;
adjusting illumination from the light of the wireless endoscope;
controlling at least the light and the camera utilizing a user interface of the second portion of the wireless endoscope controlled by a user;
capturing video utilizing the camera in communication with the lens;
formatting the video for wireless communication to a receiver associated with a display device in response to capturing the video; and
wirelessly communicating the video from a transceiver of the second portion of the wireless endoscope to the receiver in communication with the displaying device utilized to display the video.

20. The method of claim 19, further comprising:
controlling the wireless endoscope through a wireless connection to a wireless device displaying a graphical user interface for controlling the wireless endoscope.

* * * * *